US009587104B2

(12) United States Patent
Gray et al.

(10) Patent No.: US 9,587,104 B2
(45) Date of Patent: Mar. 7, 2017

(54) RELEASE MEDIA

(71) Applicant: THE UNIVERSITY OF QUEENSLAND, St. Lucia, Queensland (AU)

(72) Inventors: Peter Gray, Taringa (AU); Michael John Monteiro, Kenmore (AU); Trent Phillip Munro, Chapel Hill (AU); Andrew Benjamin James Prowse, Annerley (AU)

(73) Assignee: The University of Queensland, Queensland (AU)

( * ) Notice: Subject to any disclaimer, the term of this patent is extended or adjusted under 35 U.S.C. 154(b) by 98 days.

(21) Appl. No.: 14/406,179

(22) PCT Filed: Jun. 7, 2013

(86) PCT No.: PCT/AU2013/000610
§ 371 (c)(1),
(2) Date: Dec. 5, 2014

(87) PCT Pub. No.: WO2013/181713
PCT Pub. Date: Dec. 12, 2013

(65) Prior Publication Data
US 2015/0337128 A1 Nov. 26, 2015

(30) Foreign Application Priority Data
Jun. 7, 2012 (AU) .................. 2012902396

(51) Int. Cl.
*A61K 47/32* (2006.01)
*A61K 47/42* (2006.01)
*A61K 47/48* (2006.01)
*C08L 53/00* (2006.01)
*C08L 51/00* (2006.01)
*C12N 5/00* (2006.01)
*C08L 89/00* (2006.01)
*C12M 1/12* (2006.01)
*C08F 293/00* (2006.01)
*C08F 120/54* (2006.01)
*C08F 220/54* (2006.01)
*C12N 5/0735* (2010.01)
*C08K 5/00* (2006.01)

(52) U.S. Cl.
CPC ............ *C08L 51/003* (2013.01); *A61K 47/32* (2013.01); *A61K 47/42* (2013.01); *A61K 47/48176* (2013.01); *A61K 47/48238* (2013.01); *C08F 120/54* (2013.01); *C08F 220/54* (2013.01); *C08F 293/005* (2013.01); *C08L 89/00* (2013.01); *C12M 25/14* (2013.01); *C12N 5/0012* (2013.01); *C12N 5/0062* (2013.01); *C12N 5/0068* (2013.01); *C12N 5/0606* (2013.01); *C08F 2438/03* (2013.01); *C08K 5/0008* (2013.01); *C08L 2203/02* (2013.01); *C08L 2207/53* (2013.01);

*C12N 2509/00* (2013.01); *C12N 2513/00* (2013.01); *C12N 2523/00* (2013.01); *C12N 2533/30* (2013.01); *C12N 2533/52* (2013.01); *C12N 2539/10* (2013.01)

(58) Field of Classification Search
None
See application file for complete search history.

(56) References Cited

U.S. PATENT DOCUMENTS

| | | | |
|---|---|---|---|
| 7,160,931 B2 | 1/2007 | Cheng et al. |
| 7,193,007 B2 | 3/2007 | Cheng et al. |
| 7,718,193 B2 | 5/2010 | Stayton et al. |
| 8,512,757 B2 | 8/2013 | Yang et al. |
| 2003/0219889 A1 | 11/2003 | Sumaru et al. |
| 2003/0232430 A1 | 12/2003 | Cibelli et al. |
| 2004/0029994 A1 | 2/2004 | Cheng et al. |
| 2005/0020719 A1 | 1/2005 | Cheng et al. |
| 2005/0277739 A1 | 12/2005 | Yang et al. |
| 2007/0224241 A1 | 9/2007 | Stayton et al. |
| 2008/0160559 A1 | 7/2008 | Carre et al. |
| 2009/0137040 A1 | 5/2009 | Cibelli et al. |
| 2010/0159019 A1 | 6/2010 | Yang et al. |
| 2010/0215749 A1 | 8/2010 | Stayton et al. |
| 2011/0313066 A1 | 12/2011 | Jaber et al. |
| 2013/0102073 A1 | 4/2013 | Cibelli et al. |
| 2014/0212973 A1 | 7/2014 | Nakayama et al. |

FOREIGN PATENT DOCUMENTS

| | | |
|---|---|---|
| CA | 2427543 | 11/2004 |
| CN | 101501108 | 8/2009 |

(Continued)

OTHER PUBLICATIONS

Written Opinion of ISA for PCT/AU2013/000610, mailed Aug. 13, 2013, six pages.
Chen et al. "Thermoresponsive worms for expansion and release of human embryonic stem cells" *Biomacromolecules*, vol. 15, No. 3, pp. 844-855 (Mar. 2014).
Kataoka et al. "Application of a thermo-reversible gelation polymer, Mebiol Gel, for stem cell culture and regenerative medicine" *Journal of Stem Cells & Regenerative Medicine*, vol. 6, No. 1, pp. 10-14 (Jan. 2010).
Loh et al. "Surface coating with a thermoresponsive copolymer for the culture and non-enzymatic recovery of mouse embryonic stem cells" *Macromolecular Bioscience*, vol. 9, No. 11, pp. 1069-1079 (Nov. 2009).

(Continued)

*Primary Examiner* — Jeffrey Mullis
(74) *Attorney, Agent, or Firm* — Nixon & Vanderhye PC

(57) ABSTRACT

The present invention relates to a composition comprising polymer particles and functionalized stimulus responsive polymer; the polymer particles (i) comprising block co-polymer, and (ii) having a core-shell structure, said block co-polymer comprising (a) a non-stimulus responsive polymer block that forms at least part of the core structure, and (b) a stimulus responsive polymer block that forms at least part of the shell structure; wherein the stimulus responsive polymer of both the polymer particles and the functionalized stimulus responsive polymer are responsive to at least one common stimulus.

20 Claims, 7 Drawing Sheets

(56) References Cited

FOREIGN PATENT DOCUMENTS

| EP | 0382214 | 8/1990 |
|---|---|---|
| EP | 1365017 | 11/2003 |
| EP | 2612902 | 7/2013 |
| WO | 03/046141 | 6/2003 |
| WO | 2007/109584 | 9/2007 |
| WO | 2008/004978 | 1/2008 |
| WO | 2010/091465 | 8/2010 |
| WO | 2010/147632 | 12/2010 |
| WO | 2012/029882 | 8/2012 |
| WO | WO 2012/029882 | 8/2012 |

OTHER PUBLICATIONS

Ng et al. "A protocol describing the use of a recombinant protein-based, animal product-free medium (APEL) for human embryonic stem cell differentiation as spin embryoid bodies" *Nature Protocols*, vol. 3, No. 5, pp. 768-776 (Apr. 2008).

Supplementary European Search Report and Opinion for EP 13799995, eight pages, mailed Mar. 4, 2016.

Written Opinion of IPOS (Singapore) for SG 11201408142U six pages (Feb. 2016).

Int'l Search Report for PCT/AU2013/000610, four pages, mailed Aug. 13, 2013.

Written Opinion for PCT/AU2013/000610, six pages, mailed Aug. 13, 2013.

Kessel et al. "Mechanically driven reorganization of thermoresponsive diblock copolymer assemblies in water" *Angewandte Chemie Int'l Ed.*, vol. 50, No. 35, pp. 8082-8085 (Aug. 2011).

Nagaoka et al. "Culture of human pluripotent stem cells using completely defined conditions on a recombinant E-cadherin substratum" *BMC Developmental Biology*, vol. 10, No. 60, pp. 1-12 (Jun. 2010).

Nakayama et al. "Poly(N-isopropylacrylamide)-based smart surfaces for cell sheet tissue engineering" *Material Matters*, vol. 5, No. 3, pp. 56-61 (2010).

Nakayama et al., "Poly(N-isopropylacrylamide)-based Smart Surfaces for Cell Sheet Tissue Engineering", *Material Matters* (2010), vol. 5, No. 3, pp. 56-58.

International Search Report for PCT/AU2013/000610, mailed Aug. 13, 2013, four pages.

Notification of the Second Office Action for Chinese Application No. 201380040905.5, 24 pages, mailed Oct. 18, 2016.

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: RGD peptide

<400> SEQUENCE: 1

Gly Arg Gly Asp Ser
1               5

<210> SEQ ID NO 2
```

<211> LENGTH: 391
<212> TYPE: PRT
<213> ORGANISM: Artificial Sequence
<220> FEATURE:
<223> OTHER INFORMATION: Fibronectin type II, domains 7-10

<400> SEQUENCE: 2

```
Met Pro Leu Ser Pro Thr Asn Leu His Leu Glu Ala Asn Pro Asp
1               5                   10                  15

Thr Gly Val Leu Thr Val Ser Trp Glu Arg Ser Thr Thr Pro Asp Ile
            20                  25                  30

Thr Gly Tyr Arg Ile Thr Thr Thr Pro Thr Asn Gly Gln Gln Gly Asn
            35                  40                  45

Ser Leu Glu Glu Val Val His Ala Asp Gln Ser Ser Cys Thr Phe Asp
        50                  55                  60

Asn Leu Ser Pro Gly Leu Glu Tyr Asn Val Ser Val Tyr Thr Val Lys
65                  70                  75                  80

Asp Asp Lys Glu Ser Val Pro Ile Ser Asp Thr Ile Ile Pro Ala Val
                85                  90                  95

Pro Pro Pro Thr Asp Leu Arg Phe Thr Asn Ile Gly Pro Asp Thr Met
            100                 105                 110

Arg Val Thr Trp Ala Pro Pro Ser Ile Asp Leu Thr Asn Phe Leu
        115                 120                 125

Val Arg Tyr Ser Pro Val Lys Asn Glu Glu Asp Val Ala Glu Leu Ser
130                 135                 140

Ile Ser Pro Ser Asp Asn Ala Val Val Leu Thr Asn Leu Leu Pro Gly
145                 150                 155                 160

Thr Glu Tyr Val Val Ser Val Ser Ser Val Tyr Glu Gln His Glu Ser
                165                 170                 175

Thr Pro Leu Arg Gly Arg Gln Lys Thr Gly Leu Asp Ser Pro Thr Gly
            180                 185                 190

Ile Asp Phe Ser Asp Ile Thr Ala Asn Ser Phe Thr Val His Trp Ile
        195                 200                 205

Ala Pro Arg Ala Thr Ile Thr Gly Tyr Arg Ile Arg His His Pro Glu
210                 215                 220

His Phe Ser Gly Arg Pro Arg Glu Asp Arg Val Pro His Ser Arg Asn
225                 230                 235                 240

Ser Ile Thr Leu Thr Asn Leu Thr Pro Gly Thr Glu Tyr Val Val Ser
                245                 250                 255

Ile Val Ala Leu Asn Gly Arg Glu Glu Ser Pro Leu Leu Ile Gly Gln
            260                 265                 270

Gln Ser Thr Val Ser Asp Val Pro Arg Asp Leu Glu Val Val Ala Ala
        275                 280                 285

Thr Pro Thr Ser Leu Leu Ile Ser Trp Asp Ala Pro Ala Val Thr Val
290                 295                 300

Arg Tyr Tyr Arg Ile Thr Tyr Gly Glu Thr Gly Gly Asn Ser Pro Val
305                 310                 315                 320

Gln Glu Phe Thr Val Pro Gly Ser Lys Ser Thr Ala Thr Ile Ser Gly
                325                 330                 335

Leu Lys Pro Gly Val Asp Tyr Thr Ile Thr Val Tyr Ala Val Thr Gly
            340                 345                 350

Arg Gly Asp Ser Pro Ala Ser Ser Lys Pro Ile Ser Ile Asn Tyr Arg
        355                 360                 365

Thr Ser Asp Pro Asn Ser Ser Val Asp Lys Leu Ala Ala Ala Leu
370                 375                 380
```

Glu His His His His His
385                 390

<210> SEQ ID NO 3
<211> LENGTH: 60
<212> TYPE: PRT
<213> ORGANISM: Artificial Sequence
<220> FEATURE:
<223> OTHER INFORMATION: Vitronectin SMB domain

<400> SEQUENCE: 3

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Leu Glu His His His His His
        50                  55                  60

<210> SEQ ID NO 4
<211> LENGTH: 380
<212> TYPE: PRT
<213> ORGANISM: Artificial Sequence
<220> FEATURE:
<223> OTHER INFORMATION: recombinant GFP

<400> SEQUENCE: 4

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly Ser Asp Pro Met Val Ser Lys Gly Glu Glu Leu Phe Thr Gly
        115                 120                 125

Val Val Pro Ile Leu Val Glu Leu Asp Gly Asp Val Asn Gly His Lys
    130                 135                 140

Phe Ser Val Ser Gly Glu Gly Glu Gly Asp Ala Thr Tyr Gly Lys Leu
145                 150                 155                 160

Thr Leu Lys Phe Ile Cys Thr Thr Gly Lys Leu Pro Val Pro Trp Pro
                165                 170                 175

Thr Leu Val Thr Thr Leu Thr Tyr Gly Val Gln Cys Phe Ser Arg Tyr
            180                 185                 190

Pro Asp His Met Lys Gln His Asp Phe Phe Lys Ser Ala Met Pro Glu
        195                 200                 205

Gly Tyr Val Gln Glu Arg Thr Ile Phe Phe Lys Asp Asp Gly Asn Tyr
    210                 215                 220

Lys Thr Arg Ala Glu Val Lys Phe Glu Gly Asp Thr Leu Val Asn Arg

```
                    225                 230                 235                 240
Ile Glu Leu Lys Gly Ile Asp Phe Lys Glu Asp Gly Asn Ile Leu Gly
                245                 250                 255

His Lys Leu Glu Tyr Asn Tyr Asn Ser His Asn Val Tyr Ile Met Ala
                260                 265                 270

Asp Lys Gln Lys Asn Gly Ile Lys Val Asn Phe Lys Ile Arg His Asn
                275                 280                 285

Ile Glu Asp Gly Ser Val Gln Leu Ala Asp His Tyr Gln Gln Asn Thr
                290                 295                 300

Pro Ile Gly Asp Gly Pro Val Leu Leu Pro Asp Asn His Tyr Leu Ser
305                 310                 315                 320

Thr Gln Ser Ala Leu Ser Lys Asp Pro Asn Glu Lys Arg Asp His Met
                325                 330                 335

Val Leu Leu Glu Phe Val Thr Ala Ala Gly Ile Thr Leu Gly Met Asp
                340                 345                 350

Glu Leu Tyr Lys Lys Leu Ala Ala Gly Ser Gly Ser Gly Tyr Asp Pro
                355                 360                 365

Glu Gly Ser Gly Ser Gly His His His His His
                370                 375                 380

<210> SEQ ID NO 5
<211> LENGTH: 377
<212> TYPE: PRT
<213> ORGANISM: Artificial Sequence
<220> FEATURE:
<223> OTHER INFORMATION: recombinant mCherry

<400> SEQUENCE: 5

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
            50                  55                  60

Pro Gly Thr Ala Pro Lys Tyr Gly Ile Arg Gly Ile Pro Thr Leu Leu
65              70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly Ser Asp Pro Met Val Ser Lys Gly Glu Glu Asp Asn Met Ala
            115                 120                 125

Ile Ile Lys Glu Phe Met Arg Phe Lys Val His Met Glu Gly Ser Val
130                 135                 140

Asn Gly His Glu Phe Glu Ile Glu Gly Glu Gly Glu Gly Arg Pro Tyr
145                 150                 155                 160

Glu Gly Thr Gln Thr Ala Lys Leu Lys Val Thr Lys Gly Gly Pro Leu
                165                 170                 175

Pro Phe Ala Trp Asp Ile Leu Ser Pro Gln Phe Met Tyr Gly Ser Lys
                180                 185                 190

Ala Tyr Val Lys His Pro Ala Asp Ile Pro Asp Tyr Leu Lys Leu Ser
            195                 200                 205

Phe Pro Glu Gly Phe Lys Trp Glu Arg Val Met Asn Phe Glu Asp Gly
```

Gly Val Val Thr Val Thr Gln Asp Ser Ser Leu Gln Asp Gly Glu Phe
225                 230                 235                 240

Ile Tyr Lys Val Lys Leu Arg Gly Thr Asn Phe Pro Ser Asp Gly Pro
            245                 250                 255

Val Met Gln Lys Lys Thr Met Gly Trp Glu Ala Ser Ser Glu Arg Met
            260                 265                 270

Tyr Pro Glu Asp Gly Ala Leu Lys Gly Glu Ile Lys Gln Arg Leu Lys
        275                 280                 285

Leu Lys Asp Gly Gly His Tyr Asp Ala Glu Val Lys Thr Thr Tyr Lys
    290                 295                 300

Ala Lys Lys Pro Val Gln Leu Pro Gly Ala Tyr Asn Val Asn Ile Lys
305                 310                 315                 320

Leu Asp Ile Thr Ser His Asn Glu Asp Tyr Thr Ile Val Glu Gln Tyr
            325                 330                 335

Glu Arg Ala Glu Gly Arg His Ser Thr Gly Gly Met Asp Glu Leu Tyr
            340                 345                 350

Lys Lys Leu Ala Ala Gly Ser Gly Ser Gly Tyr Asp Pro Glu Gly Ser
        355                 360                 365

Gly Ser Gly His His His His His His
    370                 375

```
<210> SEQ ID NO 6
<211> LENGTH: 19
<212> TYPE: DNA
<213> ORGANISM: Artificial Sequence
<220> FEATURE:
<223> OTHER INFORMATION: B-actin forward primer

<400> SEQUENCE: 6
gctgtgctac gtcgccctg                                                19

<210> SEQ ID NO 7
<211> LENGTH: 15
<212> TYPE: DNA
<213> ORGANISM: Artificial Sequence
<220> FEATURE:
<223> OTHER INFORMATION: B-actin reverse primer

<400> SEQUENCE: 7
ggaggagctg gaagc                                                    15

<210> SEQ ID NO 8
<211> LENGTH: 20
<212> TYPE: DNA
<213> ORGANISM: Artificial Sequence
<220> FEATURE:
<223> OTHER INFORMATION: NANOG forward primer

<400> SEQUENCE: 8
caaaggcaaa caacccactt                                               20

<210> SEQ ID NO 9
<211> LENGTH: 20
<212> TYPE: DNA
<213> ORGANISM: Artificial Sequence
<220> FEATURE:
<223> OTHER INFORMATION: NANOG reverse primer

<400> SEQUENCE: 9
tctgctggag gctgaggtat                                               20
```

```
<210> SEQ ID NO 10
<211> LENGTH: 20
<212> TYPE: DNA
<213> ORGANISM: Artificial Sequence
<220> FEATURE:
<223> OTHER INFORMATION: OCT-4 forward primer

<400> SEQUENCE: 10
tgaagctgga gaaggagaag                                                     20

<210> SEQ ID NO 11
<211> LENGTH: 19
<212> TYPE: DNA
<213> ORGANISM: Artificial Sequence
<220> FEATURE:
<223> OTHER INFORMATION: OCT-4 reverse primer

<400> SEQUENCE: 11
atcggcctgt gtatatccc                                                      19

<210> SEQ ID NO 12
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 12
gaaggtgaag gtcggagtca                                                     20

<210> SEQ ID NO 13
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 13
aatgaagggg tcattgatgg                                                     20

<210> SEQ ID NO 14
<211> LENGTH: 20
<212> TYPE: DNA
<213> ORGANISM: Artificial Sequence
<220> FEATURE:
<223> OTHER INFORMATION: HPRT forward primer

<400> SEQUENCE: 14
gggaggccat cacattgtag                                                     20

<210> SEQ ID NO 15
<211> LENGTH: 20
<212> TYPE: DNA
<213> ORGANISM: Artificial Sequence
<220> FEATURE:
<223> OTHER INFORMATION: HPRT reverse primer

<400> SEQUENCE: 15
tcccctgttg actggtcatt                                                     20
```

RELEASE MEDIA

This application is the U.S. national phase of International Application No. PCT/AU2013/000610 filed 7 Jun. 2013 which designated the U.S. and claims priority to AU 2012902396 filed 7 Jun. 2012.

FIELD OF THE INVENTION

The present invention relates in general to release media, and in particular to compositions suitable for retaining and subsequently releasing matter such as biological material (e.g. cells, proteins, peptides etc) and drugs. Compositions in accordance with the invention are particularly suitable for use in retaining and subsequently releasing matter such as biological material and drugs, and it will therefore be convenient to describe the invention with an emphasis toward such applications. However, it is to be understood that the compositions may be used to retain and subsequently release other matter.

BACKGROUND OF THE INVENTION

There has been considerable research to date directed toward developing compositions that can retain (within and/or on) and subsequently release matter of interest. For example, drug release compositions form an important role in the medical industry. Such compositions include those where a drug is blended with polymer to form a drug/polymer composite. The polymer/drug composites may then be used as a drug release medium. For example, silicone rods comprising levonorgestrel have been used as a slow release birth control implant.

Despite release of drugs from such media being reasonably effective, there can be problems associated with the fate of a given medium after the drug has been released. For example, in the case of the levonorgestrel implant, after release of the drug the "spent" implant must be surgically removed from the subject. During removal several incisions may be required and/or the implant can fragment upon being withdrawn.

Other types of media have been developed for use in cell culture. Cell culture is typically carried out by seeding a suitable medium with cells that are to be cultured. Certain cell types, such as human embryonic stem cells (hESC) and induced pluripotent cells (iPC's), are more effectively cultured by providing a surface upon which the cells can adhere and proliferate. After adhesion and proliferation, the cultured cells need to be harvested and therefore released from the surface. Release of the cells is typically promoted by techniques such as mechanical scraping, sonication, chemical or enzymatic treatment, or a combination thereof.

Common cell release techniques can present a number of problems. For example, mechanical scraping can damage the cells, and it is often not suitable for use in confined spaces such as small diameter wells or with three dimensional structures. The use of chemical or biological agents to facilitate release of cultured cells from a given substrate can also damage the cells and/or present a risk of introducing impurities into the cultured cells. For example, a common agent such as trypsin is known to promote deterioration of cell function. Furthermore, certain cells can be particularly adherent to a given substrate and need to be subjected to forcing conditions to promote their release, the effect of which inevitably results in a degree of cell damage.

Conventional release media used in cell culture also often lack versatility in that a given medium, such as a substrate suitable for cell culture, will often not be a suitable medium for use in other applications such as drug release.

An opportunity therefore remains to develop more versatile release media that can be used in a variety of applications and/or address at least some of the problems associated with the release of matter, such as cells or drugs, from the media.

SUMMARY OF THE INVENTION

The present invention provides a composition comprising polymer particles and functionalised stimulus responsive polymer;

the polymer particles (i) comprising block co-polymer, and (ii) having a core-shell structure, said block co-polymer comprising (a) a non-stimulus responsive polymer block that forms at least part of the core structure, and (b) a stimulus responsive polymer block that forms at least part of the shell structure;

wherein the stimulus responsive polymer of both the polymer particles and the functionalised stimulus responsive polymer are responsive to at least one common stimulus.

A composition in accordance with the invention can advantageously provide for a release medium on and/or within which the functionalised stimulus responsive polymer can be retained and then released in an effective, efficient and non-invasive manner. The functionalised stimulus responsive polymer may be functionalised with a moiety such as a drug, protein or cell.

As a release medium, the components of the composition will typically be provided in a liquid. In other words, the composition may comprise the polymer particles, the functionalised stimulus responsive polymer and a liquid.

The stimulus responsive polymer of both the polymer particles and the functionalised stimulus responsive polymer can advantageously undergo a transition to exhibit different solubility in a liquid upon being subjected to a particular stimulus. For example, the stimulus responsive polymer of both the polymer particles and the functionalised stimulus responsive polymer may be a thermoresponsive polymer that is insoluble in the liquid above a given temperature and soluble in the liquid below that temperature.

Within a liquid below a temperature at which the stimulus responsive polymer of both the polymer particles and the functionalised stimulus responsive polymer are soluble, the polymer particles and the functionalised stimulus responsive polymer can present as separate entities (i.e. they are not physically associated with each other). Upon heating the liquid to or above a temperature at which the stimulus responsive polymer of both the polymer particles and the functionalised stimulus responsive polymer are insoluble, the polymer particles and the functionalised stimulus responsive polymer will associate and form an aggregate structure on and/or within which the functionalised stimulus responsive polymer is retained. This aggregate structure of the polymer particles and the functionalised stimulus responsive polymer represents the release medium from which the retained functionalised stimulus responsive polymer may be released.

To promote release of the functionalised stimulus responsive polymer from the aggregate structure, the temperature of the liquid within which the aggregate structure is located need only be lowered to a temperature at which the stimulus responsive polymer of both the polymer particles and the functionalised stimulus responsive polymer again become soluble in the liquid. In that case, solvation of the stimulus responsive polymer of both the polymer particles and the functionalised stimulus responsive polymer provides a driving force for disassociation of the aggregate structure and subsequent release of the functionalised stimulus responsive polymer.

A composition in accordance with the invention can advantageously be employed in various ways to function as a release media in, for example, cell culture and drug delivery applications.

For cell culture, the composition may function to promote aggregation of cells and comprise polymer particles, functionalised stimulus responsive polymer and a liquid. In that case the functionalised stimulus responsive polymer may be a protein functionalised stimulus responsive polymer, where the protein is capable of binding with a desired cell type.

By maintaining the temperature of the liquid below a particular temperature, say for example below 37° C., the protein functionalised stimulus responsive polymer and the polymer particles can present as separate discrete entities in the liquid, and by increasing the temperature of the liquid to 37° C. or more (i.e. applying the stimulus) the protein functionalised stimulus responsive polymer and the polymer particles will associate to form an aggregate structure.

Thus, in one embodiment the temperature of the liquid can be reduced below 37° C. A plurality of desired cells can then be introduced such that the cells bind to protein presented by the protein functionalised stimulus responsive polymer to in effect form cell functionalised stimulus responsive polymer. More than one protein functionalised stimulus responsive polymer will typically bind with each cell.

The temperature of the liquid can then be increased to 37° C. or more which will cause the now cell functionalised stimulus responsive polymer and the polymer particles to associate and form an aggregate structure. In forming the aggregate structure, cells of the cell functionalised stimulus responsive polymer will inherently form clusters, with the aggregate structure of the polymer particles and the cell functionalised stimulus responsive polymer representing a release medium from which the retained cell functionalised stimulus responsive polymer may be released.

Cells within the so formed cell clusters may then proliferate to form larger cell clusters. Proliferation of cells in this way may provide conditions that can advantageously sustain cell pluripotency and viability.

Reducing the temperature of the liquid to below 37° C. after sufficient proliferation has taken place will cause the stimulus responsive polymer of both the polymer particles and the cell functionalised stimulus responsive polymer to become soluble in the liquid. This solvation process will facilitate disassociation of the aggregate structure which in turn will assist with release of the cell functionalised stimulus responsive polymer and consequent break up of the cell clusters into smaller cell clusters and/or individual cells. In other words, a composition according to the invention advantageously enables cells to be cultured in cell clusters that can subsequently be disassembled in an effective and non-invasive manner into individual cells and/or smaller cell clusters.

As an alternative form of cell culture, the composition may comprise polymer particles, functionalised stimulus responsive polymer and a liquid, wherein the polymer particles are secured to a substrate. The secured polymer particles can present as a layer on the substrate surface. The substrate may, for example, be as a layer of mouse embryonic fibroblasts (MEF). In that case the functionalised stimulus responsive polymer may be a protein functionalised stimulus responsive polymer, where the protein is capable of binding with a desired cell type.

By maintaining the temperature of the liquid below a particular temperature, say for example below 37° C., the protein functionalised stimulus responsive polymer and the tethered polymer particles can present as separate discrete entities in the liquid, and by increasing the temperature of the liquid to 37° C. or more the protein functionalised stimulus responsive polymer and the tethered polymer particles can associate to form an aggregate structure having a protein rich surface.

Thus, in another embodiment the temperature of the liquid can be increased to 37° C. or more. This will cause the protein functionalised stimulus responsive polymer and the tethered polymer particles to associate to form an aggregate structure having a protein rich surface.

A desired cell(s) can then be introduced to the liquid whereby the cell(s) binds to protein presented at the surface of the aggregate structure. The cell(s) can then proliferate across the protein rich surface of the aggregate structure which is in effect tethered to a substrate (such as MEF), with newly formed cells also binding to protein presented at the surface of the aggregate structure. Proliferation of cells in this way may provide conditions that can advantageously sustain cell pluripotency and viability.

Reducing the temperature of the liquid to below 37° C. after sufficient proliferation has taken place will cause the stimulus responsive polymer of both the polymer particles and the now cell functionalised stimulus responsive polymer to become soluble in the liquid. This solvation process will facilitate disassociation of the aggregate structure which in turn will assist with release of the cell functionalised stimulus responsive polymer from the substrate surface. In other words, the cultured cells can advantageously be released from the substrate in an effective and non-invasive manner.

For cell culture, it is desirable that compositions of the invention are not exposed to temperatures above about 37° C. In one embodiment, subjecting the liquid to the common stimulus therefore involves heating the liquid to about 37° C. to promote aggregation of the polymer particles and the functionalised stimulus responsive polymer.

In a similar fashion, the functionalised stimulus responsive polymer may be a drug functionalised stimulus responsive polymer, and the polymer particles secured to a suitable substrate. In that case, a so formed aggregate structure of the drug functionalised stimulus responsive polymer and the polymer particles can provide for a unique drug release system.

Accordingly, in one embodiment the composition is for cell culture or drug delivery and comprises the polymer particles, the functionalised stimulus responsive polymer and a liquid.

In another embodiment, the composition is for cell culture or drug delivery and comprises the polymer particles, the functionalised stimulus responsive polymer and a liquid, wherein the polymer particles are secured to a substrate.

Compositions according to the invention can also present in the form of a gel within and/or on which the functionalised stimulus response polymer is retained. The gel can undergo a unique transformation in response to a stimulus, such as a change in temperature, to form a liquid composition (i.e. a composition in a liquid state) wherein the functionalised stimulus polymer is no longer retained and can be readily separated from the other components that make up the liquid composition. According to this embodiment, the composition further comprises a liquid, and the polymer particles are present within the liquid at a concentration that is sufficient to transform the liquid into a gel upon at least the stimulus responsive polymer of the polymer particles being subjected to the at least one common stimulus. In such an embodiment, the polymer particles will typically be free to move and aggregate with each other (i.e. they will not be tethered or secured to a fixed or non-mobile substrate).

Without wishing to be limited by theory, the polymer particles used in accordance with the invention are believed exhibit a critical gel concentration (CGC). The CGC is the concentration (in wt % relative to the combined mass of the liquid and polymer particles) of particles in the liquid at which, upon the particles being subjected to a stimulus such as a change in temperature, the polymer particles can associate with each other to form an aggregate structure that transforms the liquid state of the composition into a gel. In the context of the present invention, it will be appreciated that upon being subjected to the common stimulus the functionalised stimulus responsive polymer also aggregates with the polymer particles, and as such the functionalised stimulus responsive polymer is retained within and/or on the so formed gel. The CGC for the polymer particles will vary depending upon their morphology, and in particular the aspect ratio of the particles.

The present invention can therefore also provide a composition comprising polymer particles, functionalised stimulus responsive polymer and a liquid;

the polymer particles (i) comprising block co-polymer, and (ii) having a core-shell structure, said block co-polymer comprising (a) a non-stimulus responsive polymer block that forms at least part of the core structure, and (b) a stimulus responsive polymer block that forms at least part of the shell structure;

wherein the stimulus responsive polymer of both the polymer particles and the functionalised stimulus responsive polymer are responsive to at least one common stimulus; and wherein the polymer particles are present within the liquid at a concentration that is sufficient to transform the liquid into a gel upon at least the stimulus responsive polymer of the polymer particles being subjected to the at least one common stimulus.

Compositions in accordance with the invention that provide for a gel can also advantageously be employed in various ways to function as a release media in, for example, cell culture and drug delivery applications.

For a drug release medium, the functionalised stimulus response polymer may be functionalised with a drug and the composition provided first in the form of a liquid composition. In response to a stimulus, such as an increase in temperature, the drug functionalised stimulus responsive polymer and the polymer particles can associate to form an aggregate structure which in turn promotes transformation of the liquid into a gel. In the form of the gel, the drug functionalised stimulus responsive polymer is in effect retained within and/or on the confines of the gel. The drug can subsequently be released from the gel by subjecting the gel to a stimulus, such as a decrease in temperature, and causing it to transform back into a liquid composition, the likes of which present the drug in a "released" state.

For cell culture, the functionalised stimulus responsive polymer may be functionalised with a cell (typically formed by the protein of a protein functionalised stimulus responsive polymer binding with a cell). In that case, multiple protein functionalised stimulus responsive polymers can bind to a given cell. The composition can be provided first in the form of a liquid composition comprising a liquid, the polymer particles and the cell functionalised stimulus responsive polymer, and in response to a stimulus, such as a temperature increase, the cell functionalised stimulus responsive polymer and the polymer particles can associate to form an aggregate structure which in turn promotes a transformation of the liquid composition into a gel. In the form of the gel, the cell functionalised stimulus responsive polymer is in effect retained within and/or on the confines of the gel.

By being retained within and/or on the gel, the cell functionalised stimulus responsive polymer can function as a "seed cell" and can proliferate within and/or on the gel matrix. The gel may comprise additional functionalised stimulus responsive polymer that is functionalised with one or more moieties (e.g. proteins) that promote adherence and growth of cells. After proliferation, the cells can be released and harvested by subjecting the gel to a stimulus, such as a decrease in temperature, and causing it to transform back into a liquid composition, the effect of which releases the cells from other components of the composition making them readily available for harvesting.

Unlike conventional release media, a composition in accordance with the invention can advantageously transition from a gel into a liquid composition, the process of which promotes release of relevant matter such as drugs or cells. Notably, the transition of the gel into the liquid composition results in no residual solid or semi-solid structure remaining after release has occurred. In the context of drug release, this means that subsequent to release of the drug there is no need to retrieve any "spent" support structure. In the context of cell culturing, this means that cells can be released from the gel via non-invasive liquefaction of the gel.

The compositions are particularly versatile in that they can be readily adapted for different applications simply by selecting a different functional entity for the functionalised stimulus response polymer and/or by adjusting the concentration of the polymer particles present in the liquid.

In one embodiment, the polymer particles and functionalised stimulus responsive polymer are present in a liquid, wherein the stimulus responsive polymer associated with both the polymer particles and the functionalised stimulus responsive polymer are soluble within the liquid. In that case, the non-stimulus responsive polymer associated with the polymer particles will generally be insoluble in the liquid. For example, a composition according to the invention may comprise a hydrophilic liquid (e.g. an aqueous liquid), the polymer particles and functionalised stimulus responsive polymer, wherein the stimulus responsive polymer associated with both the polymer particles and the functionalised stimulus responsive polymer are soluble within the hydrophilic liquid. In that case, the non-stimulus responsive polymer associated with the polymer particles will generally be insoluble in the hydrophilic liquid.

In another embodiment, the composition is in the form of a gel, wherein the stimulus responsive polymer associated with both the polymer particles and the functionalised stimulus responsive polymer are insoluble within the liquid. In that case, the non-stimulus responsive polymer associated with the polymer particles will generally also be insoluble in the liquid. For example, the composition may be in the form of a gel comprising hydrophilic liquid (e.g. an aqueous liquid), wherein the stimulus responsive polymer associated with both the polymer particles and the functionalised stimulus responsive polymer are insoluble in the hydrophilic liquid. In that case, the non-stimulus responsive polymer associated with the polymer particles will generally be insoluble in the hydrophilic liquid. According to this embodiment, the polymer particles are present within the liquid at a concentration that is sufficient to transform the liquid into a gel upon at least the stimulus responsive polymer of the polymer particles being subjected to the at least one common stimulus.

The present invention also provides a cell culture system comprising the composition according to the invention. In that case, the functionalised stimulus responsive polymer may be functionalised with a cell. Such a cell culture system can advantageously not only facilitate cell culture but also provide for stimulus driven enzyme free harvesting of cells.

The present invention also provides for a drug delivery system comprising the composition according to the invention. In that case, the functionalised stimulus responsive polymer may be functionalised with a drug.

The present invention further provides a method of forming a gel comprising functionalised stimulus responsive polymer, said method comprising:
(i) providing a liquid composition comprising polymer particles, functionalised stimulus responsive polymer and a liquid;
  the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;
  wherein the stimulus responsive polymer of both the polymer particles and the functionalised stimulus responsive polymer are (a) responsive to at least one common stimulus, and (b) soluble in the liquid; and
(ii) subjecting the liquid composition to said common stimulus so as to cause the stimulus responsive polymer of both the polymer particles and the functionalised stimulus responsive polymer to transition from being soluble in the liquid to being insoluble in the liquid, wherein said transition promotes formation of the gel.

According to this embodiment, the polymer particles will of course be present within the liquid at a concentration that is sufficient to transform the liquid into a gel upon at least the stimulus responsive polymer of the polymer particles being subjected to the at least one common stimulus.

The present invention further provides a method of releasing from a gel a functionalised stimulus responsive polymer, said method comprising:
(i) providing a gel comprising polymer particles, a functionalised stimulus responsive polymer and liquid;
  the polymer particles (a) comprising block co-polymer, and (b) having a core-shell structure, said block co-polymer comprising (a) a non-stimulus responsive polymer block that forms at least part of the core structure and (b) a stimulus responsive polymer block that forms at least part of the shell structure;
  wherein the stimulus responsive polymer of both the polymer particles and the functionalised stimulus responsive polymer are (a) responsive to at least one common stimulus, and (b) insoluble in the liquid; and
(ii) subjecting the gel to said common stimulus so as to cause the stimulus responsive polymer of both the polymer particles and the functionalised stimulus responsive polymer to transition from being insoluble in the liquid to being soluble in the liquid, wherein said transition causes the gel to become a liquid composition comprising the polymer particles, the functionalised stimulus responsive polymer and the liquid, thereby promoting release of the functionalised stimulus responsive polymer from the gel.

According to the methods of the invention, in one embodiment the liquid is a hydrophilic liquid, for example an aqueous liquid.

According to the method of releasing from the gel a functionalised stimulus responsive polymer, in one embodiment the functionalised stimulus responsive polymer is functionalised with a cell. In a further embodiment, the functionalised stimulus responsive polymer is functionalised with a drug.

Further aspects and/or embodiments of the invention are described in more detail-below.

BRIEF DESCRIPTION OF THE DRAWINGS

Embodiments of the invention will hereinafter be illustrated by way of example only with reference to the accompanying drawings in which:

FIG. 1A shows the polymer particles having a rod-like shape, and FIG. 1B show the polymer particles have a spherical shape;

Figure 1:
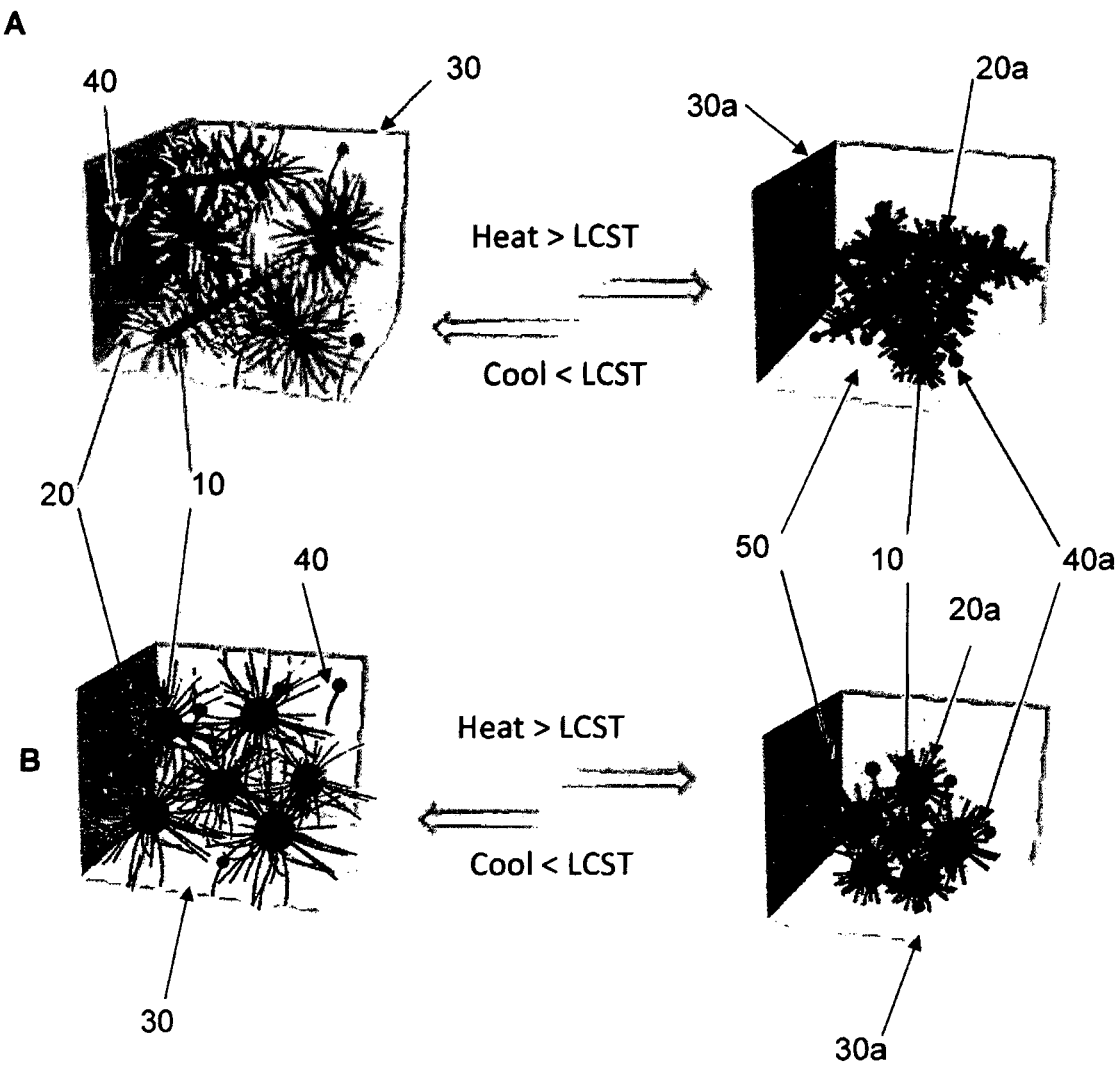
FIG. 1 schematically illustrates a composition in accordance with the invention comprising polymer particles, functionalised stimulus responsive polymer and a liquid.

Some Figures contain colour representations or entities. Coloured versions of the Figures are available upon request.

DETAILED DESCRIPTION OF THE INVENTION

A composition in accordance with the invention comprises polymer particles. The polymer particles have a core-shell structure as herein described. Provided the polymer particles have the required core-shell structure and can be used as described herein, there is no particular limitation regarding their shape or size.

The polymer particles may have a spherical, ellipsoidal, hoop, cylindrical, rod, or worm like shape. The polymer particles may comprise a mixture of different shaped polymer particles.

In one embodiment, all dimensions of the polymer particles are less than about 1 micron.

In a further embodiment, at least one dimension of the polymer particles is less than about 100 nm, or less than about 70 nm, or less than about 50 nm, or less than about 30 nm, or less than about 20 nm, or less than about 15 nm, or less than about 10 nm.

In another embodiment, the polymer particles have an aspect ratio (average length:average diameter) greater than 1, for example at least 5, or at least 10, or at least 20, or at least 30, or at least 40, or at least 60, or at least 80, or at least 100, or at least 500. The aspect ratio of the polymer particles may range from about 5 to about 1000 or from about 25 to about 500, or about 50 to about 200.

The core-shell structure of the polymer particles comprises block co-polymer. By "block co-polymer" is meant a co-polymer that is a block polymer having adjacent blocks that are constitutionally different. By having a "core-shell" structure is meant that the polymer particles have an inner composition (the core) that is surrounded by a substantially different outer composition (the shell). In the context of the present invention, the "shell" is defined by the stimulus polymer block of the block co-polymer. This stimulus polymer block may be soluble or insoluble relative to a liquid within which the polymer particles are located. The "core" is defined by the non-stimulus polymer block of the block co-polymer and will typically be insoluble relative to a liquid within which the polymer particles are located.

Thus, the block co-polymer that forms the polymer particles comprises a non-stimulus responsive polymer block and a stimulus responsive block, whereby the non-stimulus responsive polymer block forms at least part of the core structure of the polymer particles and the stimulus responsive polymer block forms at least part of the shell structure of the polymer particles. The polymer particles may therefore be described as having a core comprising non-stimulus responsive polymer and a shell comprising stimulus responsive polymer where the transition from the core to the shell corresponds to a transition from the non-stimulus responsive polymer block of the co-polymer to the stimulus responsive polymer block of the co-polymer.

An important feature of the block co-polymer is the stimulus responsive polymer block. Stimulus responsive polymers (also known as "smart" polymers) are polymers which undergo a physical or chemical change in response to stimuli such as a change in temperature, pH, ionic strength and/or wavelength of light.

The physical or chemical change exhibited by stimulus responsive polymer in response to a given stimulus can vary depending upon the type of polymer employed. For example, one form of physical change is where in response to a stimulus the polymer undergoes a reversible transition from being hydrophobic in character to being hydrophilic in character.

In one embodiment, the stimulus responsive polymer block of the block co-polymer is of a type that upon being subjected to a stimulus undergoes a transition from being hydrophobic in character to being hydrophilic in character or vice versa.

In a further embodiment, the stimulus responsive polymer block of the block co-polymer is a temperature responsive polymer block that in response to a change in temperature undergoes a physical or chemical transition.

In yet a further embodiment, the stimulus responsive polymer block of the block co-polymer is a temperature responsive polymer that in response to a change in temperature undergoes a transition from being hydrophobic in character to being hydrophilic in character or vice versa.

Those skilled in the art will appreciate that expressions such as "hydrophobic in character" and "hydrophilic in character" are generally used in the art to convey favourable or unfavourable interactions between one substance relative to another (e.g. attractive or repulsive interactions) and not to define absolute qualities of a particular substance. For example, hydrophilic materials are more likely to be wetted or dissolved by an aqueous medium (attractive interaction), whereas hydrophobic materials are less, likely to be wetted or dissolved by an aqueous medium (repulsive interaction). Unless otherwise stated, in the context of the present invention these expressions are intended to be a reference to the polarity of the stimulus responsive polymer relative to the polarity of an aqueous liquid. Thus, by being hydrophilic in character the stimulus responsive polymer can be wetted or dissolved by an aqueous liquid. By being hydrophobic in character the stimulus responsive polymer can not be wetted or dissolved by an aqueous liquid.

The stimulus responsive polymer block of the block co-polymer may be in the form of a homopolymer or a co-polymer.

The stimulus responsive polymer block of the block co-polymer may be a natural polymer or a synthetic polymer.

Examples of temperature responsive polymers include homopolymer and co-polymers of N-isopropyl acrylamide (NIPAAm, NIPAm, or NIPAM).

Poly(N-isopropyl acrylamide) homopolymer (P(NIPAAm), PNIPAm, PNIPAM or pNIPAM) is a well known temperature responsive polymer and exhibits a lower critical solution temperature (LCST) of about 36° C. in an aqueous medium. It can reversibly assume (i) an expanded random coil structure below the LCST that is hydrophilic in character and readily wetted or solvated by an the aqueous liquid, and (ii) a collapsed globular structure above the LCST that is hydrophobic in character and not readily wetted or solvated by an aqueous liquid.

When NIPAAm is co-polymerised with one or more hydrophilic ethylenically unsaturated comonomers such as acrylamide, the LCST of the resulting co-polymer, can be raised relative to that of P(NIPAAm). The opposite may occur when NIPAAm is co-polymerised with one or more hydrophobic comonomers, such as N-t-butyl acrylamide. Co-polymers of NIPAAm with hydrophilic monomers such as acrylamide have a higher LCST and generally a broader temperature range of precipitation (relative to P(NIPAAm)), while co-polymers of NIPAAm with hydrophobic monomers such as N-t-butyl acrylamide have a lower LCST (relative to P(NIPAAm) and are generally more likely to retain the sharp transition characteristic of P(NIPAAm).

Examples of pH responsive polymers include those derived from pH responsive vinyl monomers such as acrylic acid, methacrylic acid, and other alkyl-substituted acrylic acids, maleic anhydride, maleic acid, 2-acryamido-2-methyl-1-propanesulfonic acid, N-vinyl formamide, N-vinyl acetamide, aminoethyl methacrylate, phosphoryl ethyl acrylate or methacrylate. pH responsive polymers may also be prepared as polypeptides from amino acids (e.g. polylysine or polyglutiamic acid) all derived from naturally occurring polymers such as proteins (e.g. lysozyme, albumin, casein), or polysaccharides (e.g. alginic acid, hyaluronic acid, carrageenan, chitosan, carboxymethyl, cellulose) or nucleic acids such as DNA. pH responsive polymers usually comprise pendant pH sensitive functional groups such as —OPO$(OH)_2$, —COOH or —NH$_2$.

By co-polymerising a monomer that gives rise to a temperature responsive polymer such as NIPAAm with a small amount (e.g. less than about 10 mole %) of a comonomer that gives rise to a pH responsive polymer such as acrylic acid, the resulting co-polymer can display both temperature and pH responsiveness. The LCST of such a co-polymer can remain unaffected, sometimes even lowered a few degrees, at a pH where the co-polymer is not ionised, but the LCST can be dramatically raised if the pH sensitive groups become ionised. When pH sensitive groups are present at a high concentration, the LCST response of the temperature responsive effect may be for all practical purposes eliminated.

Block co-polymers derived from pH and temperature responsive monomers can be prepared such that they retain both pH and temperature transitions independently. For example, a block co-polymer having a pH responsive block (polyacrylic acid) and a temperature responsive block (P(NIPAAm)) can retain independent pH and temperature responsiveness.

The stimulus responsive polymer block of the block co-polymer may therefore itself be a block co-polymer.

In one embodiment, the stimulus responsive polymer block of the block co-polymer is not in itself a block co-polymer.

Examples of light responsive polymers include those that contain chromophoric groups pendant to or along the main chain of the polymer and, when exposed to an appropriate wavelength of light, can be isomerised from a trans to a cis form, which can be dipolar and more hydrophilic and promote reversible polymer conformational changes. Other light sensitive groups can also be converted by light stimulation from a relatively non-polar hydrophobic, non-ionised state to a hydrophilic ionic state.

In the case of pendant light-sensitive groups such as a light-sensitive dye (e.g. aromatic azo compounds or stilbene derivatives), they may be conjugated to a reactive monomer (an exception is a dye such as chlorophyllin, which already comprises a vinyl group) and then homopolymerised or co-polymerised with one or more other monomers, including temperature responsive or pH responsive monomers. The light sensitive group may also be conjugated to an end of a polymer chain, including a stimulus responsive polymer chain. Techniques for conjugating such light sensitive groups to monomers or polymer chains are known.

Generally, a light responsive polymer will be prepared from vinyl monomers that contain light-sensitive pendant groups. Such monomers may be homopolymerised or co-polymerised with one or more other ethylenically unsaturated monomers.

The light-sensitive groups may be dye molecules that isomerise or become ionised when they absorb certain wavelength of light, converting them from hydrophobic to hydrophilic confirmations or vice versa, or they may be dye molecules which give off heat when they absorb certain wavelength of light. In the former case, the isomerisation alone can cause chain expansion or collapse, while in the later case the polymer can precipitate if it is also temperature responsive.

Examples of chromophoric groups that may give rise to the light responsive properties include aromatic diazo dyes. When a dye of this type is exposed to 350-410 nm UV light, the trans form of the dye, which is hydrophobic in character, can be isomerised to its cis form, which is dipolar and more hydrophilic in character, this in turn can cause polymer conformational changes. Exposure of the dye to visible light at about 750 nm can reverse this phenomenon.

Examples of specific ion responsive polymers include polysaccharides such as carrageenan that change their confirmation, for example, from a random to an ordered confirmation, as a function of exposure to ions such as $K^+$ or $Ca^{2+}$. Other examples of specific ion responsive polymers include polymers with pendant ion chelating groups such histidine or EDTA.

As indicated above, stimulus responsive polymers may be responsive to multiple stimuli. For example, if a light responsive polymer is also temperature responsive, a UV or visible light stimulated conversion of a chromophor conjugated along the polymer backbone to a more hydrophobic or hydrophilic confirmation can also stimulate the dissolution/wetting or precipitation of the polymer, depending upon the polymer composition and temperature. Alternatively, if the chromophor absorbs light and converts it to thermal energy rather than stimulating isomerisation, then the localised heating can also stimulate a phase change in a temperature responsive polymer such as P(NIPAAm) when the system temperature is near the phase separation temperature. The incorporation of multiple sensitivities through the co-polymerisation of appropriate monomers can lend greater versatility to the stimulus responsive polymers used in accordance with the invention.

Provided that the stimulus responsive polymer block of the block co-polymer provides for the polymer particles used in accordance with the invention, there is no particular limitation regarding the number average molecular weight of the stimulus responsive polymer block. The number average molecular weight of the stimulus responsive polymer block will generally fall within the range of about 1,500 to about 40,000, for example from about 2,000 to about 20,000, or from about 2,000 to about 10,000.

Reference to the number average molecular weight of a polymer referred to herein is that which is determined by size exclusion chromatography (SEC).

It can also be convenient to refer to the block length of the stimulus responsive polymer block in terms of the number of polymerised monomer residues that form the block. In that case, the stimulus responsive polymer block will generally comprise from about 20 to 200, or from about 30 to about 150, or from about 40 to about 80 polymerised monomer units.

The block co-polymer that forms the polymer particles also comprises a non-stimulus responsive polymer block. By a "non-stimulus responsive polymer block" is meant a polymer block that would not be considered by those skilled in the art to be a stimulus responsive polymer block and as such not undergo a physical or chemical change in response to stimuli such as a change in temperature, pH, ionic strength and/or wavelength of light.

The non-stimulus responsive polymer block may be in the form of a homopolymer or a co-polymer.

The non-stimulus responsive polymer block may be a natural polymer or a synthetic polymer.

The non-stimulus responsive polymer block may comprise a polymerised residue of a monomer type that has the required properties to provide for a stimulus responsive polymer. However, in that case, the amount of such polymerised monomer residue will be insufficient to impart stimulus responsive properties to the polymer block.

In one embodiment, the non-stimulus responsive polymer block does not contain polymerised monomer residue of a type that can provide for a stimulus responsive polymer.

Provided that the non-stimulus responsive polymer block of the block co-polymer provides for the polymer particles used in accordance with, the invention, there is no particular limitation regarding the number average molecular weight of the non-stimulus responsive polymer block. The number average molecular weight of the non-stimulus responsive polymer block will generally fall within the range of about 500 to about 40,000, for example from about 2,000 to about 20,000, or from about 4,000 to about 10,000.

The non-stimulus responsive polymer block and the stimulus responsive polymer block of the block co-polymer will generally be prepared via the polymerisation of suitable ethylenically unsaturated monomers. The monomers used to prepare the block co-polymer will of course be appropriately selected to provide for the non-stimulus responsive and stimulus responsive polymer blocks, respectively. Such monomers will also generally be capable of being polymerised with other monomers. The factors which determine co-polymerisability of various monomers are well documented in the art. For example, see: Greenlee, R. Z., in Polymer Handbook 3$^{rd}$ Edition (Brandup, J., and Immergut. E. H. Eds) Wiley: New York, 1989 p II/53.

Suitable ethylenically unsaturated monomers that may be polymerised to prepare the block co-polymer include those of formula (I):

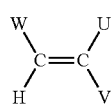

(I)

where U and W are independently selected from —$CO_2H$, —$CO_2R^1$, —$COR^1$, —$CSR^1$, —$CSOR^1$, —$COSR^1$, —$CONH_2$, —$CONHR^1$, —$CONR^1_2$, hydrogen, halogen and optionally substituted $C_1$-$C_4$ alkyl or U and W form together a lactone, anhydride or imide ring that may itself be optionally substituted, where the optional substituents are independently selected from hydroxy, —$CO_2H$, —$CO_2R^1$, —$COR^1$, —$CSR^1$, —$CSOR^1$, —$COSR^1$, —$CN$, —$CONH_2$, —$CONHR^1$, —$CONR^1_2$, —$OR^1$, —$SR^1$, —$O_2CR^1$, —$SCOR^1$, and —$OCSR^1$;

V is selected from hydrogen, $R^1$, —$CO_2H$, —$CO_2R^1$, —$COR^1$, —$CSR^1$, —$CSOR^1$, —$COSR^1$, —$CONH_2$, —$CONHR^1$, —$CONR^1_2$, —$OR^1$, —$SR^1$, —$O_2CR^1$, —$SCOR^1$, and —$OCSR^1$;

where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain.

The or each $R^1$ may also be independently selected from optionally substituted $C_1$-$C_{22}$ alkyl, optionally substituted $C_2$-$C_{22}$ alkenyl, optionally substituted $C_2$-$C_{22}$ alkynyl, optionally substituted $C_6$-$C_{18}$ aryl, optionally substituted $C_3$-$C_{18}$ heteroaryl, optionally substituted $C_3$-$C_{18}$ carbocyclyl, optionally substituted $C_2$-$C_{18}$ heterocyclyl, optionally substituted $C_7$-$C_{24}$ arylalkyl, optionally substituted $C_4$-$C_{18}$ heteroarylalkyl, optionally substituted $C_7$-$C_{24}$ alkylaryl, optionally substituted $C_4$-$C_{18}$ alkylheteroaryl, and an optionally substituted polymer chain.

$R^1$ may also be selected from optionally substituted $C_1$-$C_{18}$ alkyl, optionally substituted $C_2$-$C_{18}$ alkenyl, optionally substituted aryl, optionally substituted heteroaryl, optionally substituted carbocyclyl, optionally substituted heterocyclyl, optionally substituted aralkyl, optionally substituted heteroarylalkyl, optionally substituted alkaryl, optionally substituted alkylheteroaryl and a polymer chain.

In one embodiment, $R^1$ may be independently selected from optionally substituted $C_1$-$C_6$ alkyl.

Examples of optional substituents for $R^1$ include those selected from alkyleneoxidyl (epoxy), hydroxy, alkoxy, acyl, acyloxy, formyl, alkylcarbonyl, carboxy, sulfonic acid, alkoxy- or aryloxy-carbonyl, isocyanato, cyano, silyl, halo, amino, including salts and derivatives thereof. Examples polymer chains include those selected from polyalkylene oxide, polyarylene ether and polyalkylene ether.

Examples of monomers of formula (I) include maleic anhydride, N-alkylmaleimide, N-arylmaleimide, dialkyl fumarate and cyclopolymerisable monomers, acrylate and methacrylate esters, acrylic and methacrylic acid, styrene, N-alkylacrylamides, acrylamide, methacrylamide, and methacrylonitrile, mixtures of these monomers, and mixtures of these monomers with other monomers.

Further examples of monomers of formula (I) include: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N-isopropylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, ethylene and chloroprene. This list is not exhaustive.

In one embodiment, the block co-polymer comprises a non-stimulus responsive polymer block derived from one or more monomers selected from styrene, 4-methylstyrene and n-butyl acrylate.

In a further embodiment, the block co-polymer comprises a stimulus responsive polymer block derived from one or more monomers selected from N-isopropylacrylamide and monomethoxyl ether poly(ethylene oxide) acrylate.

In a further embodiment, the block co-polymer comprises a polystyrene non-stimulus polymer block and a poly(N-isopropylacrylamide) stimulus responsive polymer block.

Provided that the polymer particles have the required block co-polymer composition, there is no particular limitation on the method by which they may be prepared.

The polymer particles may, for example, be prepared according to methodology outlined in WO 2010/091465, the entire contents of which are incorporated herein by cross-reference. In that case, the polymer particles may be prepared using conventional dispersion polymerisation techniques (e.g. conventional emulsion, mini-emulsion and suspension polymerisation) and equipment.

For example, the polymer particles may be prepared by a method that comprises providing a dispersion having a continuous aqueous phase, a dispersed organic phase comprising one or more ethylenically unsaturated monomers, a stimulus responsive polymer having a controlled radical polymerisation moiety covalently bound thereto, and a stabiliser for the organic phase. Having prepared the dispersion, the one or more ethylenically unsaturated monomers are polymerised under the control of the controlled radical polymerisation moiety.

The one or more ethylenically unsaturated monomers used are selected so as to provide for a non-stimulus responsive polymer block. Accordingly, the polymerisation provides for a block copolymer comprising a non-stimulus responsive polymer block and a stimulus responsive polymer block.

By being polymerised "under the control" of the controlled radical polymerisation moiety is meant that polymerisation of the monomers proceeds via the appropriate controlled radical polymerisation mechanism to form polymer. The controlled radical polymerisation moiety is therefore a moiety that can participate in controlled or mediate the radical polymerisation of one or more ethylenically unsaturated monomers according to a particular type of controlled radical polymerisation so as to form a polymer chain.

Examples of controlled radical polymerisation include iniferter polymerisation, stable free radical mediated polymerisation (SFRP), atom transfer radical polymerisation (ATRP), and reversible addition fragmentation chain transfer (RAFT) polymerisation. For example, where the controlled radical polymerisation moiety is a RAFT moiety, the polymerisation of the monomers will proceed via a RAFT mechanism to form polymer.

Such polymerisation provides for a dispersion of polymer particles comprising block co-polymer chains having a stimulus responsive polymer block and a non-stimulus responsive polymer block. By subjecting the so formed polymer particles to an appropriate stimulus (i.e. a stimulus that causes the stimulus responsive polymer block of the block co-polymer to undergo a chemical or physical transition), the polymer particles can undergo a morphogenic transformation to form a variety polymer particles with different morphologies. For example, where the stimulus responsive polymer used in the polymerisation comprises a temperature responsive stimulus polymer block, the resulting polymer particles may be provided with a rod or worm like shape by subjecting the dispersion of polymer particles to heating/cooling cycles above and below the LCST of the stimulus responsive polymer block.

Confirmation of the various shapes of polymer particles formed may be established using a conventional analytical technique such as Transmission Electron Microscopy (TEM).

In addition to the polymer particles, the composition in accordance with the invention also comprises functionalised stimulus responsive polymer. By the expression "functionalised stimulus responsive polymer" is meant stimulus responsive polymer having attached to it by physical or chemical association (e.g. a covalent bond) a functional entity that is to be released from a release medium according to the invention. There is no particular limitation regarding the nature of such a functional entity provided that it, or a modified or derived form thereof, can be released from the release medium.

For example, the functionalised stimulus responsive polymer may be functionalised with a functional entity selected from biological material, drugs, and cell receptor ligand.

Examples of biological material include, but are not limited to, cells, proteins, peptides, nucleic acids, lipids and carbohydrates.

Examples of cell receptor ligands include, but are not limited to, proteins, peptides, neurotransmitters, hormones, drugs, agonists and antagonists.

Specific examples of cells include, but are not limited to, Embryonic stem cells (hESCs), Mesenchymal stem cells (MSCs), Hematopoietic stem cells (HSCs), Neural stem cells (NSCs), Cancer Stem Cells (CSCs), Induced pluripotent stem cells, Adult stem cells, Foetal Stem Cells, Tissue specific stem cells, Umbilical Cord Stem Cells, Placenta Derived Stem Cells, Chinese Hamster Ovary Cells (CHO), Baby Hamster Kidney Cells (BHK), human amniocytes, NS0 cells, PER.C6 cells, Madin-Darby canine kidney cell (MDCK), Hybridoma Cells, Human embryonic kidney cells (HEK), Muscovy Duck (AGE.CR®), Vero cells (African green monkey), NIH-3T3, MRC-5, WI-38, FRhl-2, chicken embryo fibroblasts (CEF), chicken embryo kidney (CEK) and blastoderm-derived embryonic stem cells (e.g., EB14, Vivalis), insect cells (eg Sf9 and High Five), HeLa cells, COS cells, and primary or immortalised human cells.

Specific examples of proteins include, but are not limited to, extracellular matrix components and proteoglycans e.g. Vitronectin, Laminin, Collagen, Fibronectin and Elastin.

Specific examples of peptides include, but are not limited to, cell adhesion motifs including RGD, YIGSR, REDV and poly-alanine, and thrombopoietin (TPO) derived peptides.

Specific examples of drugs include, but are not limited to, Aphidicolin, Blebbistatin, Colchicine, Cytochalasin, Latrunculin, Leptomycin, ROCK Inhibitor (Y-27632), glycogen synthase kinase 3 inhibitors (e.g. BIO (6-bromoindirubin-3'-oxime) and CHIR99021), RA (retinoic acid), Pluripotin/SC1, PD0325901, A83-01, IDE1, (−) Indolactam V, Stauprimide, SB431542, BIX-01294, RG108, (+)Bayk 8644, Parnate, Kenpaullone, Valproic Acid, Reversine and phorbol myristate acetate.

The stimulus responsive polymer component of the functionalised stimulus responsive polymer may be a stimulus responsive polymer as herein described. The functional entity and the stimulus responsive polymer may be chemically or physically associated with each other using techniques known in the art. For example, the functional entity and the stimulus responsive polymer may each be provided with complimentary reactive functional groups that undergo chemical reaction to provide for a covalent bond between the functional entity and the stimulus responsive polymer.

Compositions in accordance with the invention may comprise liquid. When the composition is a liquid composition, the stimulus responsive polymer associated with both the polymer particles and the functionalised stimulus responsive polymer are soluble within the liquid. To prevent the polymer particles from dissolving entirely in the liquid, the non-stimulus responsive polymer block of the co-polymer that forms the polymer particle core will of course be insoluble within the liquid.

In one embodiment, the liquid is a hydrophilic liquid, such as an aqueous liquid.

In addition to selecting the stimulus responsive polymer associated with the polymer particles and the functionalised stimulus responsive polymer to have a desired solubility in the liquid, the respective stimulus responsive polymers are also selected to be responsive to at least one common stimulus. In other words, the respective stimulus responsive polymers can undergo a physical or chemical change in response to the same stimulus. For example, the stimulus responsive polymer of both the polymer particles and the functionalised stimulus responsive polymer may be temperature responsive polymers.

Generally, the stimulus responsive polymer of both the polymer particles and the functionalised stimulus responsive polymer will not only be responsive to at least one common stimulus, but both stimulus responsive polymers will respond to that common stimulus in the same or a similar manner. For example, where the stimulus responsive polymer of both the polymer particles and the functionalised stimulus responsive polymer are temperature responsive polymers, they will both have the same or a similar LSCT.

In one embodiment, the stimulus responsive polymer of both the polymer particles and the functionalised stimulus responsive polymer (a) are temperature responsive polymers, and (b) have an LSCT that differs by no more than 5° C., or 4° C., or 3° C., or 2° C., or 1° C.

When the stimulus responsive polymer associated with both the polymer particles and the functionalised stimulus responsive polymer is soluble in the liquid, the functionalised stimulus responsive polymer and the polymer particles present within the liquid composition as discrete separate entities (i.e. they do not aggregate).

Provided that the composition can function as intended, there is no particular limitation regarding the liquid that can be used. In one embodiment the liquid is a hydrophilic liquid, such as an aqueous liquid, water soluble alcohol or polyether such as polyethylene oxide. As an aqueous liquid, the water may comprise one or more water soluble liquids or solids.

With reference to FIG. 1, FIGS. 1A and 1B schematically illustrates a composition according to the invention comprising polymer particles, functionalised stimulus responsive polymer and liquid. FIG. 1A illustrates polymer particles having a rod-like shape, and FIG. 1B illustrates polymer particles having a spherical shape. The compositions are illustrated with reference to a temperature below an LCST (to the left) and above an LCST (to the right).

With particular reference to FIG. 1A (left hand side), the polymer particles have a core (10) and a shell (20) that are respectively formed from polymer blocks of a block copolymer. A non-stimulus responsive polymer block (10) forms at least part of the core (10) and is insoluble in the liquid (30). A stimulus responsive polymer block (20) forms at least part of the shell (20). The number of stimulus responsive polymer blocks (20) shown has been restricted for clarity. In this example, the stimulus responsive polymer blocks (20) of the polymer particles are thermoresponsive polymer blocks and are at a temperature below their LCST so they are soluble in the liquid (30). The polymer particles present as discrete entities in the liquid. The composition also comprises functionalised stimulus responsive polymer (40). In this example, the stimulus responsive polymer of the functionalised stimulus responsive polymer is a thermoresponsive polymer and at a temperature below its LCST is also soluble in the liquid (30). The functionalised stimulus responsive polymers also present as discrete entities in the liquid.

With particular reference to FIG. 1A (right hand side), the temperature of the liquid (30a) has been increased to above the LCST. This applied stimulus causes the thermoresponsive polymer of both the polymer particles and the functionalised stimulus responsive polymer to become insoluble in the liquid (30a), which in turn causes the polymer particles and the functionalised stimulus responsive polymer to form an aggregate structure (50). In the aggregate structure, the polymer particles comprise (i) a non-stimulus responsive polymer block (10) that forms at least part of the core (10) which is insoluble in the liquid (30a), and (ii) a stimulus responsive polymer block (20a) that forms at least part of the shell (20a) which is also now insoluble in the liquid (30a). In the aggregate structure, the thermoresponsive polymer of the functionalised stimulus responsive polymer is also insoluble in the liquid (30a) and associates with the polymer particles to form the aggregate structure (50). The functionalised stimulus responsive polymer can be released from the aggregate structure (50) simply by cooling the temperature of the liquid (30a) to below the LCST.

A similar consideration applies to FIG. 1B, except in that case the polymer particles have a spherical shape.

There is no particular limitation regarding the amount of polymer particles and functionalised stimulus responsive polymer, or the ratio of polymer particles to functionalised stimulus responsive polymer, that may be used in the compositions of the invention. The amount and ratio used will typically be governed by the intended application and can be readily determined by those skilled in the art.

Where the compositions are to be used in the formation of a gel, they will comprise a liquid and the polymer particles are present within the liquid at a concentration that is sufficient to transform the liquid into a gel upon at least the stimulus responsive polymer of the polymer particles being subjected to the at least one common stimulus. To form the gel the polymer particles are provided such that they can readily associate with each other and develop an aggregate structure (i.e. form a collection of particles in physical communication with each other).

The CGC for a given type of polymer particle will vary primarily depending on the aspect ratio of the particles. To form the gel the polymer particles will be provided at or above their CGC. Polymer particles with a low aspect ratio will typically have a higher CGC than those particles with a high aspect ratio. For example, polymer particles with an aspect ratio of 10 may have a CGC of around 5-10 wt %, whereas polymer particles with an aspect ratio of 100 may have a CGC of around 0.1-0.5 wt %. Those skilled in the art will be able to readily determine the CGC for a given polymer particle or mixture of polymer particles.

By the term "gel" is meant an apparent solid like mass have a jelly like consistency that does not exhibit typical liquid flow characteristics. A composition in accordance with the invention presenting in the form of a "gel" will comprise the polymer particles, the stimulus responsive polymer and a liquid.

Without wishing to be limited by theory, it is believed that causing (through applying a stimulus) the stimulus responsive polymer of the polymer particles to undergo a physical or chemical transition, for example from being soluble in the liquid to being insoluble in the liquid, can lead to the formation of three dimensional aggregated structures of the particles. Where the polymer particles are present at or above their CGC this aggregation is believed to give rise to a percolated particle network which in turn causes the composition to transition from being in a liquid state into the gel.

Also without wishing to be limited by theory, it is believed that causing (through applying a stimulus) the stimulus responsive polymer of the functionalised stimulus responsive polymer to undergo a physical or chemical transition, for example from being soluble in the liquid to being insoluble in the liquid, leads to the functionalised stimulus responsive polymer forming an aggregated structure with the polymer particles (having also undergone a similar transition). This in turn in effect binds the functionalised stimulus responsive polymer to the aggregate structure (i.e. to form the release medium), which depending on the concentration of the polymer particles may or may not form part of a gel.

For example, a composition in accordance with the invention may comprise polymer particles and functionalised stimulus responsive polymer within an aqueous liquid. The block co-polymer of the polymer particles may comprise (a) a hydrophobic non-stimulus responsive polymer block that forms at least part of the core structure and is insoluble within the aqueous liquid, and (b) a thermo-responsive polymer block that forms at least part of the shell structure, and below it's LCST is soluble within the aqueous liquid. The functionalised stimulus responsive polymer may be a functionalised thermo-responsive polymer, with the thermo-responsive polymer (a) having the same LCST as the thermo-responsive polymer block that forms at least part of the shell structure, and (b) below it's LCST is soluble within the aqueous liquid. At a temperature below the LCST the polymer particles and the functionalised thermo-responsive polymer present as separate and discrete entities.

Subjecting the liquid to an increase in temperature above the LCST of the thermo-responsive polymer of both the polymer particles and the functionalised thermo responsive polymer causes the hydrophilic character of the thermo-responsive polymer to transition from being soluble in the aqueous liquid to being hydrophobic in character and insoluble in the aqueous liquid. This transition causes the polymer particles and functionalised thermo-responsive polymer to associate and form an aggregate structure.

Formation of the aggregate structure gives rise to a release medium from which the functionalised thermo-responsive polymer or a modified form thereof can subsequently be released.

Development of fully defined conditions for reproducible, large-scale production of hESC remains significant challenge for widespread therapeutic application. In other cell-based manufacturing industries, such as production of biopharmaceuticals, the cells used can be grown as monodispersed suspension cultures at large-scale (10,000-20,000 L) in stirred tank bioreactors. hESC, however, are yet to be readily adapted to suspension culture and require adherence to a biologically active substrate for high viability, long-term growth and expansion, while maintaining their undifferentiated state, limiting clinical and commercial use.

hESCs are typically derived from the inner cell mass of a 5-6-day old blastocyst of a fertilized embryo. They possess two important characteristics: (1) the ability to proliferate indefinitely while maintaining a stable karyotype, and (2) the ability to differentiate into somatic cells from all four adult cell lineages (ectoderm, mesoderm, endoderm and the germ cells). However, for these applications to become a reality, it is important to develop robust, scalable and standardized systems to produce initially, undifferentiated hESC expansion followed by highly efficient differentiation to the lineage of interest. Reproducible expansion of undifferentiated hESC or induced pluripotent stem cells (iPSC, together collectively termed pluripotent stem cells, PSC) in quantities sufficient for lineage specific differentiation is expected to provide a powerful system for subsequent use in cell therapy or drug discovery.

The response of any given PSC cell line to a culture condition can be influenced by a number of factors including lot-to-lot variability of media components, genetic variability, whether the line is hESC or iPSC and specifically regarding iPSC, and whether the iPSC have in fact been de-differentiated to an equivalent developmental stage as their hESC cousins.

Not all PSCs are created equal. In fact, what constitutes a PSC is consistently evolving, from the first derivation of hESC in 1998 to the generation of iPSC in 2006 and the recent discovery of $Oct4^+$, pluripotent cells in the mammary glands. In addition, hESC have always been compared to mouse embryonic stem cells (mESC) with many key differences between the two that were thought, at one point, to stem from the fact they were cell lines from different species. However, recent research suggests hESC may be similar to mouse epiblast stem cells and the difference between mESC and hESC was due to hESC being slightly further along the developmental pathway. With such variables in mind, a major issue becomes generating a reproducible culture system capable of cell expansion for multiple cell lines.

The issue of reproducibility can also be considered in the context of media composition and the extracellular matrix (ECM). The concerns regarding lot-to-lot variability and potential immunogenic response to cells grown in or on animal derived components is known in the literature. As such, culture processes for PSC have progressed from the fetal bovine serum (FBS) containing media, mouse feeder layer co-culture system originally used for hESC derivation to systems that utilise increasingly defined media formulations. The efficiency and utilisation of defined media is reliant on effective selection of attachment matrices usually based on mouse derived ECM mixtures Matrigel or Geltrex. Recently, advances have been made in replacing these animal derived components with fully defined substrates consisting of either recombinant proteins like laminin, vitronectin, fibronectin and E-cadherin or simple polymers decorated with small peptides.

Reports have shown that laminin-511 is able to maintain long-term pluripotent expansion of hESCs with stable karyotype in mTeSR1 media compared to other laminins which include laminin-332, laminin-411 and laminin-111. Another ECM protein well-studied and characterised in its support of pluripotent hESC expansion is vitronectin (VN). Other studies have shown hESC maintenance is capable with a short, recombinantly produced fragment of the VN somatomedin B domain followed by the arginine-glycine-aspartic acid (RGD) motif responsible for association with cell surface integrins and cell binding. Further studies have highlighted some of the variations in the response of hESC to ECM constitution by recombinantly producing fragments of VN comprised of different VN domains showing that under their specific growth conditions, the RGD motif and heparin binding domains gave the best response from hESC in regards to attachment and growth.

The importance of cell-cell and cell-ECM contact has also been demonstrated in a recent set of studies in which it was shown 1) a role for Rho kinases and myosin in embryonic cell-cell signalling, 2) that enzymatic dissociation of hESC led to fatal disruption of cell surface E-cadherin and integrin signalling, and 3) that actin-myosin contraction post enzymatic dissociation is responsible for increased cell death through tissue disorganisation (Anoikis). Enzymatic digestion can destroy cell surface integrins and growth factor receptors responsible for important survival and pluripotency maintenance signalling pathways. The ability to culture hESC using non-enzymatic methods and appropriate selection of surface substrate is critical for the future of stem cells in therapeutic applications.

However, such systems/advances in ECM constitution are limited in their scalability due to the restrictions of 2D culture.

To overcome this, 3D suspension systems may be a suitable option as they allow reproducible, controllable automation for mass production of high quality cells, at the same time eliminating labor-intensive and time-consuming methods involved with adherent culture vessels.

However, expansion of PSCs in 3D systems can be problematic in that firstly, PSC are grown in a cluster of cells termed embryoid bodies (EB) which were originally utilised for PSC differentiation. Second, the requirement for cell-cell contact in PSC cultures as outlined above make single cell or small cluster expansion of PSCs prone to high rates of cell death, 50% or higher, even in the presence of inhibitors of actin-myosin induced anoikis. Thirdly, if EBs or PSC aggregates are required for 3D expansion, the aggregate size needs to be closely controlled as this impacts on the behaviour of the cells in terms of growth and pluripotent status.

Finally, PSC expansion requires reproducibility such that clinically relevant numbers of cells are attained for efficient differentiation to the cell type of interest. For example cardiomyocytes, to treat a patient with myocardial infarction, the hypothetical number of cardiomyocytes required has been estimated at approximately $1-2\times10^9$ cells. Current use of mini-bioreactors or suspended embryoid bodies for differentiation cultures have reported low yields of cardiomyocyte generation from $3.1\times10^4$ to $1.1\times10^5$ cardiomyocytes per ml.

With these factors in mind, conventional PSC, 3D expansion techniques utilise media that contain one or more undefined components, use enzymatic or other passage methods that subsequently require cell death inhibitors, or maintain low expansion rates no better than 2D equivalents limiting the potential for scale up.

The present invention provides a unique solution to at least some of the problems with hPSC culture. Compositions according to the invention can offer excellent biocompatibility and allow cellular growth and subsequent non-enzymatic release of cells using an applied non-invasive stimulus.

The unique compositions according to the invention can offer advantages over conventional cell culture compositions/techniques, including: 1) the inclusion of different growth factors or ECM fragments that can be tuned on demand, 2) non-invasive stimuli can be used to promote release of the cells, which is gentler on the cells, thereby removing the need for enzymes or ROCKi, and 3) composition is easily transferable between 2D and 3D environments thus making it applicable for therapeutic applications.

In one embodiment for cell culture, a composition in accordance with the invention may comprise polymer particles and functionalised stimulus responsive polymer within an aqueous liquid. The block co-polymer of the polymer particles may comprise (a) a hydrophobic non-stimulus responsive polymer block that forms at least part of the core structure and is insoluble within the aqueous liquid, and (b) a thermo-responsive polymer block that forms at least part of the shell structure, and below it's LCST is soluble within the aqueous liquid. The functionalised stimulus responsive polymer may be a functionalised thermo-responsive polymer, with the thermoresponsive polymer (a) having the same LCST as the thermo-responsive polymer block that forms at least part of the shell structure, and (b) below it's LCST is soluble within the aqueous liquid. At a temperature below the LCST the polymer particles and the functionalised thermo-responsive polymer present as separate and discrete entities.

Subjecting the liquid to an increase in temperature above the LCST of the thermo-responsive polymer of both the polymer particles and the functionalised thermo responsive polymer causes the hydrophilic character of the thermo-responsive polymer to transition from being soluble in the aqueous liquid to being hydrophobic in character and insoluble in the aqueous liquid. This transition causes the polymer particles and functionalised thermo-responsive polymer to associate and form an aggregate structure.

Formation of the aggregate structure gives rise to a release medium from which the functionalised thermo-responsive polymer or a modified form thereof can subsequently be released.

Where the polymer particles are secured to a substrate, the so formed release medium can present on the surface of that substrate. For example, the polymer particles may be secured to a substrate such as a layer of mouse embryonic fibroblasts (MEF). The functionalised thermo-responsive polymer in that case may be a protein functionalised thermo-responsive polymer, where the protein is capable of binding with a desired cell type. When the liquid is below the LCST, the polymer particles and the protein functionalised thermo-responsive polymer will present as discrete separate entities.

Upon heating the liquid to or above the LCST, the protein functionalised thermo-responsive polymer will aggregate onto and be retained by the tethered polymer particles so as to form an aggregate structure that serves as the release medium. In that state, the surface of the polymer particles may be replete with protein from the protein functionalised thermo-responsive polymer. One or more cells capable of binding with the protein component of the protein functionalised stimulus responsive can then be introduced to the liquid. The one or more cells may then bind with the protein and proliferate across this protein rich surface, with new cells also binding with the proteins. Proliferation of cells in this way may provide conditions that can advantageously sustain cell pluripotency and viability.

Reducing the temperature of the liquid to below the LCST after sufficient proliferation has taken place can promote disassociation of the aggregate structure which in turn can facilitate release of the now cell functionalised thermo-responsive polymer. In other words, the cultured cells can advantageously be released for harvest from the substrate in an effective and non-invasive manner.

Examples of such substrates include, glass, metal, ceramic, plastic, feeder cells (e.g. fibroblasts such as mouse embryonic fibroblasts, and combinations thereof.

In one embodiment, the present invention therefore provides a method of culturing cells, said method comprising:
  (i) providing a liquid composition comprising a liquid, polymer particles secured to a substrate and cell receptor ligand functionalised stimulus responsive polymer;
    the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;
    wherein the stimulus responsive polymer of both the polymer particles and the cell receptor ligand functionalised stimulus responsive polymer are (a) responsive to at least one common stimulus, and (b) soluble in the liquid;
  (ii) subjecting the liquid composition to said common stimulus so as to cause the stimulus responsive polymer of both the polymer particles and the cell receptor ligand functionalised stimulus responsive polymer to transition from being soluble in the liquid to being insoluble in the liquid, wherein said transition promotes aggregation of the polymer particles and the cell receptor ligand functionalised stimulus responsive polymer to form an aggregate structure with a surface comprising the cell receptor ligand;
  (iii) introducing to the liquid one or more cells that are to be cultured such that it or they bind with a cell receptor ligand; and
  (iv) culturing cells upon said surface comprising the cell receptor ligand.

This method may further comprise a step of:
  (v) subjecting the liquid composition comprising the cultured cells to said common stimulus so as to cause the stimulus responsive polymer of both the polymer particles and the cell receptor ligand functionalised stimulus responsive polymer to transition from being insoluble in the liquid to being soluble in the liquid, wherein said transition facilitates release of said cultured cells.

This method may also further comprise a step of
  (vi) removing from the liquid composition at least some of the cultured cells formed in step (v).

This method may also further comprise a step of
  (vii) repeating one or more of steps (i)-(v) after step (vi) so as to culture further cells upon said surface comprising cell receptor ligand.

In a further embodiment, the present invention also provides a method of culturing cells, said method comprising:
  (i) providing a gel composition comprising a liquid, polymer particles and cell receptor ligand functionalised stimulus responsive polymer;
    the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;
    wherein the stimulus responsive polymer of both the polymer particles and the cell functionalised stimulus responsive polymer are (a) responsive to at least one common stimulus, and (b) insoluble in the liquid;
  (ii) introducing to the gel one or more cells that are to be cultured such that it or they bind with a cell receptor ligand; and
  (iii) culturing cells on and/or within the gel.

This method may further comprise a step of:
  (iv) subjecting the gel comprising the cultured cells to said common stimulus so as to cause the stimulus responsive polymer of both the polymer particles and the cell receptor ligand functionalised stimulus responsive polymer to transition from being insoluble in the liquid to being soluble in the liquid, wherein said transition facilitates release of said cultured cells.

This method may also further comprise a step of:
  (v) removing from the liquid composition at least some of the cultured cells formed in step (iv).

This method may also further comprise a step of:
  (vi) repeating one or more of steps (i)-(iv) after step (v) so as to culture further cells on and/or within the gel.

Where the polymer particles are free to move (i.e. they are not secured to a fixed or non-mobile substrate), by maintaining the temperature of the liquid below the LCST the functionalised thermo-responsive polymer and the polymer particles will present as separate discrete entities in the liquid, and by increasing the temperature of the liquid above the LCST the functionalised thermo-responsive polymer and the polymer particles will associate to form three dimensional aggregate structures. The functionalised thermo-responsive polymer in that case may also be a protein functionalised thermo-responsive polymer, where the protein is capable of binding with a desired cell type.

In that case, when the temperature of the liquid is below the LCST a plurality of desired cells can be introduced such that the cells bind to protein presented by the protein functionalised thermo-responsive polymer to in effect form cell functionalised thermo responsive polymer. More than one protein functionalised thermo-responsive polymer will typically, bind with each cell.

The temperature of the liquid can then be increased to above the LCST which will cause the now cell functionalised thermo-responsive polymer and the polymer particles to associate and form an aggregate structure. In forming the aggregate structure, cells of the cell functionalised thermoresponsive polymer will inherently form clusters, with the aggregate structure of the polymer particles and the cell functionalised thermo-responsive polymer representing a release medium from which the retained cell functionalised thermo-responsive polymer may be released.

Cells within the so formed cell clusters may then proliferate to form larger cell clusters. Proliferation of cells in this way may provide conditions that can advantageously sustain cell pluripotency and viability.

Reducing the temperature of the liquid to below the LCST after sufficient proliferation has taken place can promote disassociation of the aggregate structure which in turn can facilitate release of the cell functionalised thermo-responsive polymer and consequent break up of the cell clusters. In other words, the composition according to the invention advantageously enables cells to be cultured in cell clusters dispersed within a liquid where the cultured cell clusters can subsequently be broken up into individual cells and/or smaller cell clusters in an effective and non-invasive manner.

According to this form of the invention, once the cultured cell clusters have been broken down into individual cells and/or smaller cell clusters, additional protein functionalised thermo-responsive polymer can be introduced at a temperature below the LCST and the cell culture process repeated. In this way cells can advantageously cultured and harvested in a continuous cyclic process.

In one embodiment, the present invention therefore provides a method of culturing cells, said method comprising:
(i) providing a liquid composition comprising a liquid, polymer particles and cell functionalised stimulus responsive polymer;
   the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;
   wherein the stimulus responsive polymer of both the polymer particles and the cell functionalised stimulus responsive polymer are (a) responsive to at least one common stimulus, and (b) soluble in the liquid;
(ii) subjecting the liquid composition to said common stimulus so as to cause the stimulus responsive polymer of both the polymer particles and the cell functionalised stimulus responsive polymer to transition from being soluble in the liquid to being insoluble in the liquid, wherein said transition promotes aggregation of the polymer particles and the cell functionalised stimulus responsive polymer to form cell clusters; and
(iii) culturing cells within and/or on said cell clusters.

This method may further comprise a step of:
(iv) subjecting the liquid composition comprising the cultured cells to said common stimulus so as to cause the stimulus responsive polymer of both the polymer particles and the cell functionalised stimulus responsive polymer to transition, from being insoluble in the liquid to being soluble in the liquid, wherein said transition facilitates release from said cell clusters of individual cells and/or smaller cell clusters.

This method may also further comprise a step of:
(v) removing from the liquid composition at least some of the so formed individual cells and/or smaller cell clusters formed in step (iv).

This method may also further comprise a step of:
(vi) repeating one or more of steps (i)-(iv) after step (v) so as to culture further cells within and/or on the so formed cell clusters.

Methods of culturing cells according to the invention can advantageously be performed continuously such that cells can be repeatedly cultured and then harvested.

Where the polymer particles are present within the liquid at a concentration equal to or above the particles CGC, upon heating the liquid above the LCST the liquid will instead be transformed into a gel and cell culture may alternatively be conducted as herein described.

Thus, in the form of a gel composition the invention can advantageously be used to retain matter such as drugs and/or biological material that present as the functional entity of the functionalised stimulus responsive polymer.

Where the functional entity of the functionalised stimulus responsive polymer is a drug, the composition in the form of a gel can advantageously be used as a release media for that drug. Such a drug release media may be provided in any desired shape, for example with the gel taking on the shape of the container within which the gel was formed.

Gel formed using the composition of the invention has excellent stability and can be maintained in a gel state for days, months and even years.

Provided a given drug also has adequate stability, a composition according to the invention in the form of a gel which comprises the drug can also advantageously remain in a stable gel state for days, months and even years.

Where the composition in accordance with the invention is to be used for cell culture, the functional entity of the functionalised stimulus responsive polymer used will generally be a cell receptor ligand such as a protein that can bind with the cell(s) of interest. A combination of different receptor ligand functionalised stimulus responsive polymers may be used. For example, one or more receptor ligands may be selected to provide for a particular function. Generally, a selected receptor ligand will at the very least be capable of binding to a cell. However, a given receptor ligand may also be selected to promote survival and/or proliferation of a cell (e.g. growth factor proteins).

In one embodiment, the functionalised stimulus responsive polymer used in accordance with the invention is a cell receptor ligand functionalised stimulus responsive polymer.

A composition in accordance with the invention in the form of the gel might be prepared using a cell receptor ligand functionalised stimulus responsive polymer, whereby the cell receptor ligand is selected such that it can bind with a desired cell(s). Seed cells can then be introduced to the formed gel such that they migrate and bind with the cell receptor ligand of the cell receptor ligand functionalised stimulus responsive polymer. The resulting gel can then be used to culture the cells.

Alternatively, at least some of such cell receptor ligand functionalised stimulus responsive polymer can first be bound to a cell(s) prior to forming the gel, and the resulting cell functionalised stimulus responsive polymer, optionally in conjunction with cell receptor ligand functionalised stimulus responsive polymer, used in forming the gel. In that case, cell functionalised stimulus responsive polymer (to function as a seed cell), optionally in conjunction with cell receptor ligand functionalised stimulus responsive polymer, is contained and subsequently retained within the gel upon its formation. The resulting gel can then be used for cell culture.

Where the compositions are to be used in the formation of a gel for cell culture, that gel may be formed on a substrate (as herein described), and cells allowed to proliferate within and/or on the gel. Upon forming a gel in accordance with the invention, the gel can advantageously adhere to the surface upon which the gel is formed. For example, the gel may be formed within a plastic container. In that case, the so formed gel can advantageously adhere to the surface of that container.

Cell receptor ligand functionalised stimulus responsive polymer used in accordance with the invention may be prepared using techniques known in the art. For example, the cell receptor ligand may be a protein and the stimulus responsive polymer-protein conjugate can be prepared using a S—S coupling reaction.

A given cell may bind with more than one cell receptor ligand functionalised stimulus responsive polymer chains. Equally, a given cell receptor ligand functionalised stimulus responsive polymer chain may bind with more than one cell.

Cells may be cultured in accordance with the invention using conventional cell culture methodology. For example, cells may be cultured in both 2D and 3D formats.

Compositions in accordance with the invention can advantageously allow cells to maintain pluripotency during cell growth and expansion. The compositions achieve this at least in part by providing a support for the cells to aggregate in either static or suspension culture. The compositions can also be designed to incorporate the required cellular cues to maintain the pluripotent state, for example through integrin signalling and interaction with integrin binding molecules.

An important feature of the invention is that upon forming the aggregate structure of the polymer particles and functionalised stimulus responsive polymer, the functionalised stimulus responsive polymer can be released from that structure by subjecting the structure to a stimulus, such as a change in temperature. It will be appreciated that the functional entity of the functionalised stimulus responsive polymer used at the outset to form the aggregate structure may or may not present in the same form at the time of being released from aggregate structure.

For example, the functional entity of the functionalised stimulus responsive polymer may be a drug, and it is this drug functionalised stimulus responsive polymer that is ultimately released from the aggregate structure.

As a further example, the functional entity of the functionalised stimulus responsive polymer may be a cell receptor ligand. Where the composition is used for cell culture, that cell receptor ligand may bind with a cell during cell culture and the functionalised stimulus responsive polymer might then best be described as a cell functionalised stimulus responsive polymer. In that case, the cell receptor ligand functionalised stimulus responsive polymer is still released from the aggregate structure albeit in a modified form with a cell attached to it.

In one embodiment, the functionalised stimulus responsive polymer is provided with a biodegradable coupling between the functional entity (e.g. drug or cell receptor ligand) and the stimulus responsive polymer such that upon release from the release medium the biodegradable coupling degrades and the functional entity is cleaved from the stimulus responsive polymer.

Where the compositions in accordance with the invention are used for cell culture, release of cell functionalised stimulus responsive polymer from the aggregate structure can be promoted by, for example, subjecting the aggregate structure to a stimulus, such as lowering it's temperature, whereby the stimulus responsive polymer of both the polymer particles and the functionalised stimulus responsive polymer become soluble in the liquid within which the aggregate structure is contained. Release of cell functionalised stimulus responsive polymer can also be facilitated by application of mechanical shear stress.

In this specification "optionally substituted" is taken to mean that a group may or may not be substituted or fused (so as to form a condensed polycyclic group) with one, two, three or more of organic and inorganic groups, including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino (NH$_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate, phosphate, triarylmethyl, triarylamino, oxadiazole, and carbazole groups. Optional substitution may also be taken to refer to where a —CH$_2$— group in a chain or ring is replaced by a group selected from —O—, —S—, —NR$^a$—, —C(O)— (i.e. carbonyl), —C(O)O— (i.e. ester), and —C(O)NR$^a$— (i.e. amide), where R$^a$ is as defined herein.

Preferred optional substituents include alkyl, (e.g. C$_{1-6}$ alkyl such as methyl, ethyl, propyl, butyl, cyclopropyl, cyclobutyl, cyclopentyl or cyclohexyl), hydroxyalkyl (e.g.

hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)CH$_3$), phenylamino (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), 0-C(O)-alkyl (e.g. $C_1$. 6alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$alkyl, and amino), replacement of CH$_2$ with C=O, CO$_2$H, CO$_2$alkyl (e.g. $C_{1-6}$ alkyl such as methyl ester, ethyl ester, propyl ester, butyl ester), CO$_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONH$_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl) aminoalkyl (e.g., HN$C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS$C_{1-6}$ alkyl-), carboxyalkyl (e.g., HO$_2$C$C_{1-6}$ alkyl-), carboxyesteralkyl (e.g., $C_{1-6}$ alkylO$_2$C$C_{1-6}$ alkyl-), amidoalkyl (e.g., H$_2$N(O)C$C_{1-6}$ alkyl-, H($C_{1-6}$ alkyl)N(O)C$C_{1-6}$ alkyl-), formylalkyl (e.g., OHC$C_{1-6}$alkyl-), acylalkyl (e.g., $C_{1-6}$ alkyl(O)C$C_{1-6}$ alkyl-), nitroalkyl (e.g., O$_2$N$C_{1-6}$ alkyl-), sulfoxidealkyl (e.g., R(O)S$C_{1-6}$ alkyl, such as $C_{1-6}$ alkyl(O)S$C_{1-6}$ alkyl-), sulfonylalkyl (e.g., R(O)$_2$S$C_{1-6}$ alkyl- such as $C_{1-6}$ alkyl(O)$_2$S$C_{1-6}$ alkyl-), sulfonamidoalkyl (e.g., $_2$HRN(O)S$C_{1-6}$ alkyl, H($C_{1-6}$ alkyl)N(O)S$C_{1-6}$ alkyl-), triarylmethyl, triarylamino, oxadiazole, and carbazole.

As used herein, the term "alkyl", used either alone or in compound words denotes straight chain, branched or cyclic alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", butyl" etc, it will be understood that this can refer to any of straight, branched and cyclic isomers where appropriate. An alkyl group may be optionally substituted by one or more optional substituents as herein defined.

The term "alkenyl" as used herein denotes groups formed from straight chain, branched or cyclic hydrocarbon residues containing at least one carbon to carbon double bond including ethylenically mono-, di- or polyunsaturated alkyl or cycloalkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethylenically mono-, di- or polyunsaturated alkyl or cycloalkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

The term "halogen" ("halo") denotes fluorine, chlorine, bromine or iodine (fluoro, chloro, bromo or iodo).

The term "aryl" (or "carboaryl") denotes any of single, polynuclear, conjugated and fused residues of aromatic hydrocarbon ring systems (e.g. $C_{6-24}$ or $C_{6-18}$). Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may or may not be optionally substituted by one or more optional substituents as herein defined. The term "arylene" is intended to denote the divalent form of aryl.

The term "carbocyclyl" includes any of non-aromatic monocyclic, polycyclic, fused or conjugated hydrocarbon residues, preferably $C_{3-20}$ (e.g. $C_{3-10}$ or $C_{3-8}$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl. A carbocyclyl group may be optionally substituted by one or more optional substituents as herein defined. The term "carbocyclylene" is intended to denote the divalent form of carbocyclyl.

The term "heteroatom" or "hetero" as used herein in its broadest sense refers to any atom other than a carbon atom which may be a member of a cyclic organic group. Particular examples of heteroatoms include nitrogen, oxygen, sulfur, phosphorous, boron, silicon, selenium and tellurium, more particularly nitrogen, oxygen and sulfur.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazolyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl. A heterocyclyl group may be optionally substituted by one or more optional substituents as herein defined. The term "heterocyclylene" is intended to denote the divalent form of heterocyclyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, and furazanyl. A heteroaryl group may be optionally substituted by one or more optional substituents as herein defined. The term "heteroarylene" is intended to denote the divalent form of heteroaryl.

The term "acyl" either alone or in compound words denotes a group containing the moiety C=O (and not being a carboxylic acid, ester or amide) Preferred acyl includes C(O)—$R^e$, wherein $R^e$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The $R^e$ residue may be optionally substituted as described herein.

The term "sulfoxide", either alone or in a compound word, refers to a group —S(O)$R^f$ wherein $R^f$ is selected from hydrogen, alkyl, alkenyl, alkynyl, aryl, heteroaryl, heterocyclyl, carbocyclyl, and aralkyl. Examples of preferred $R^f$ include $C_{1-20}$alkyl, phenyl and benzyl.

The term "sulfonyl", either alone or in a compound word, refers to a group S(O)$_2$—$R^f$, wherein $R^f$ is selected from hydrogen, alkyl, alkenyl, alkynyl, aryl, heteroaryl, heterocyclyl, carbocyclyl and aralkyl. Examples of preferred $R^f$ include $C_{1-20}$alkyl, phenyl and benzyl.

The term "sulfonamide", either alone or in a compound word, refers to a group S(O)NR$^f$R$^f$ wherein each R$^f$ is independently selected from hydrogen, alkyl, alkenyl, alkynyl, aryl, heteroaryl, heterocyclyl, carbocyclyl, and aralkyl. Examples of preferred R$^f$ include $C_{1-20}$alkyl, phenyl and benzyl. In one embodiment at least one R$^f$ is hydrogen. In another embodiment, both R$^f$ are hydrogen.

The term, "amino" is used here in its broadest sense as understood in the art and includes groups of the formula NR$^a$R$^b$ wherein R$^a$ and R$^b$ may be any independently selected from hydrogen, alkyl, alkenyl, alkynyl, aryl, carbocyclyl, heteroaryl, heterocyclyl, arylalkyl, and acyl. R$^a$ and R$^b$, together with the nitrogen to which they are attached, may also form a monocyclic, or polycyclic ring system e.g. a 3-10 membered ring, particularly, 5-6 and 9-10 membered systems. Examples of "amino" include NH$_2$, NHalkyl (e.g. $C_{1-20}$alkyl), NHaryl (e.g. NHphenyl), NHaralkyl (e.g. NHbenzyl), NHacyl (e.g. NHC(O)$C_{1-20}$alkyl, NHC(O)phenyl), Nalkylalkyl (wherein each alkyl, for example $C_{1-20}$, may be the same or different) and 5 or 6 membered rings, optionally containing one or more same or different heteroatoms (e.g. O, N and S).

The term "amido" is used here in its broadest sense as understood in the art and includes groups having the formula C(O)NR$^a$R$^b$, wherein R$^a$ and R$^b$ are as defined as above. Examples of amido include C(O)NH$_2$, C(O)NHalkyl (e.g. $C_{1-20}$alkyl), C(O)NHaryl (e.g. C(O)NHphenyl), C(O)NHaralkyl (e.g. C(O)NHbenzyl), C(O)NHacyl (e.g. C(O)NHC(O)$C_{1-20}$alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula $CO_2R^g$, wherein $R^g$ may be selected from groups including alkyl, alkenyl, alkynyl, aryl, carbocyclyl, heteroaryl, heterocyclyl, aralkyl, and acyl. Examples of carboxy ester include $CO_2C_{1-20}$alkyl, $CO_2$aryl (e.g. $CO_2$phenyl), $CO_2$aralkyl (e.g. $CO_2$ benzyl).

As used herein, the term "aryloxy" refers to an "aryl" group attached through an oxygen bridge. Examples of aryloxy substituents include phenoxy, biphenyloxy, naphthyloxy and the like.

As used herein, the term "acyloxy" refers to an "acyl" group wherein the "acyl" group is in turn attached through an oxygen atom. Examples of "acyloxy" include hexylcarbonyloxy (heptanoyloxy), cyclopentylcarbonyloxy, benzoyloxy, 4-chlorobenzoyloxy, decylcarbonyloxy (undecanoyloxy), propylcarbonyloxy (butanoyloxy), octylcarbonyloxy (nonanoyloxy), biphenylcarbonyloxy (eg 4-phenylbenzoyloxy), naphthylcarbonyloxy (eg 1-naphthoyloxy) and the like.

As used herein, the term "alkyloxycarbonyl" refers to an "alkyloxy" group attached through a carbonyl group. Examples of "alkyloxycarbonyl" groups include butylformate, sec-butylformate, hexylformate, octylformate, decylformate, cyclopentylformate and the like.

As used herein, the term "arylalkyl" refers to groups formed from straight or branched chain alkanes substituted with an aromatic ring. Examples of arylalkyl include phenylmethyl (benzyl), phenylethyl and phenylpropyl.

As used herein, the term "alkylaryl" refers to groups formed from aryl groups substituted with a straight chain or branched alkane. Examples of alkylaryl include methylphenyl and isopropylphenyl.

The present invention will hereinafter be further described with reference to the following non-limiting examples.

EXAMPLES

Materials

Solvents used were HPLC or AR grade. Activated basic alumina (Aldrich: Brockmann I, standard grade, ~150 mesh, 58 Å), MilliQ water, sodium dodecyl sulphate (SDS: Aldrich, 99%) were used as received. Styrene (STY: Aldrich, >99%) was passed through a basic alumina column to remove inhibitor. N-isopropylacrylamide (NIPAM: Aldrich, 97%) was recrystallised from hexane, Azobisisobutyronitrile (AIBN: Riedel-de Haen) from methanol prior to use. Carbondisulfide (99%), 1-butanethiol (99%), methyl bromopropionate (98%), dimethyl sulfoxide (DMSO, >99.9%), Aldrithil™-2 (98%), hexylamine (99%) were used as received from Aldrich. Triethyleneamine (>99%) was used as received from MERCK. hESC lines MEL1 (male) and MEL2 (female) were provided by Stem Core Queensland (Formerly Australian Stem Cell Centre) and routinely maintained as manually passaged cultures on mouse embryonic fibroblast feeder layers under approval from the Australian National Health and Medical Research Council (Licence No. 309709). Media used in all experimentation was StemPro® serum free media for hESC (Life Technologies Carlsbad, Calif., USA). Controls were seeded onto tissue culture plastic dishes (BD Falcon) coated for one hour in 1:200 Geltrex™.

Analytical Techniques

Size Exclusion Chromatography (SEC)

SEC measurements were performed using a Waters Alliance 2690 Separations Module equipped with an autosampler, Differential Refractive Index (RI) detector and a Photo Diode Array (PDA) detector connected in series. HPLC grade tetrahydrofuran was used as eluent at flow rate 1 mL/min. The columns consisted of two 7.8×300 mm Waters linear Ultrastyragel SEC columns connected in series. Polystyrene standards were used for calibration.

Transmission Electron Microscopy (TEM)

The nanostructure appearance of the polymer latex was analyzed using a JEOL-1010 transmission electron microscope utilizing an accelerating voltage of 100 kV with spot size 6 at ambient temperature. A typical TEM grid preparation was as follows: A polymerization mixture was diluted with Milli-Q water to approximately 0.05 wt %. A formvar pre-coated copper TEM grid was then dipped in the diluted latex solution and dried on filter paper at 25° C.

1H Nuclear Magnetic Resonance (NMR) Spectroscopy

All NMR spectra were recorded on a Bruker DRX 500 MHz spectrometer.

Matrix-Assisted Laser Desorption Ionization-Time-of-Flight (MALDI-ToF) Mass Spectrometry MALDI-ToF MS spectra were obtained using a Bruker MALDI-ToF autoflex III smart beam equipped with a nitrogen laser (337 nm, 200 Hz maximum firing rate) with a mass range of 600-400,000 Da. Spectra were recorded in both reflectron mode (2,000-5,000 Da) and linear mode (5,000-20,000 Da). Trans-2-[3-(4-tert-butylphenyl)-2-methyl-propenylidene]malononitrile (DCTB; 20 mg/mL in THF) was used as the matrix and Na(CF3COO) (1 mg/mL in THF) as the cation source. Samples were prepared by co-spotting the matrix (20 µL), Na(CF3COO) (1 µL), and polymer (20 µL, 1 mg/mL in THF) solutions on the target plate.

Cells were adapted to single cell passage using TrypLE (Life Technologies) enzymatic digestion. Cells were detached from the tissue culture surface using TrypLE (Life Technologies) and plated on glass coverslips (inserted into 24 well plates) or organ culture dishes coated with pNIPAM/PSTY diblock copolymer functionalised with either Vitronectin, Fibronectin or RGD peptide (Table 1) in StemPro® (Life Technologies). Cells were seeded at $5 \times 10^4$ cells/coverslip or organ culture dish for attachment assays and $1 \times 10^6$ for cell sheet formation. For binding controls, organ culture dishes and coverslips were coated with Geltrex™ (Life Technologies) diluted 1:200 in DMEM-F12. Images were taken on an EVOS$_{fl}$ inverted microscope (Advanced Microscopy Group, Bothell Wash.) at 20× magnification and cells counted manually using a standard haemocytometer. For temperature dependant detachment cells were released from the surface by incubation at room temperature or 4° C. with gentle agitation. Cell sheets were released from the pNIPAM/PSTY diblock copolymer ECM functionalised surface 24 hrs post seeding.

TABLE 1

Recombinant protein fragment sequences

| Protein or Peptide Fragment | Sequence |
|---|---|
| RGD | GRGDS (SEQ ID NO: 1) |
| Fibronectin Type II, domains 7-10 | MPLSPPTNLHLEANPDTGVLTVSWERSTTPDITGY RITTTPTNGQQGNSLEEVVHADQSSCTFDNLSPGL EYNVSVYTVKDDKESVPISDTIIPAVPPPTDLRFT NIGPDTMRVTWAPPPSIDLTNFLVRYSPVKNEEDV AELSISPSDNAVVLTNLLPGTEYVVSVSSVYEQHE STPLRGRQKTGLDSPTGIDFSDITANSFTVHWIAP RATITGYRIRHHPEHFSGRPREDRVPHSRNSITLT NLTPGTEYVVSIVALNGREESPLLIGQQSTVSDVP RDLEVVAATPTSLLISWDAPAVTVRYYRITYGETG GNSPVQEFTVPGSKSTATISGLKPGVDYTITVYAV TGRGDSPASSKPISINYRTSDPNSSSVDKLAAALE HHHHHH (SEQ ID NO: 2) |

TABLE 1-continued

Recombinant protein fragment sequences

| Protein or Peptide Fragment | Sequence |
|---|---|
| Vitronectin SMB domain | MDQESCKGRCTEGFNVDKKCQCDELCSYYQSCCTD YTAECKPQVTRGDVFTMLEHHHHHH (SEQ ID NO: 3) |
| GFP | MSDKIIHLTDDSFDTDVLKADGAILVDFWAEWCGP CKMIAPILDEIADEYQGKLTVAKLNIDQNPGTAPK YGIRGIPTLLLFKNGEVAATKVGALSKGQLKEFLD ANLAGSGSGSDPMVSKGEELFTGVVPILVELDGDV NGHKFSVSGEGEGDATYGKLTLKFICTTGKLPVPW PTLVTTLTYGVQCFSRYPDHMKQHDFFKSAMPEGY VQERTIFFKDDGNYKTRAEVKFEGDTLVNRIELKG IDFKEDGNILGHKLEYNYNSHNVYIMADKQKNGIK VNFKIRHNIEDGSVQLADHYQQNTPIGDGPVLLPD NHYLSTQSALSKDPNEKRDHMVLLEFVTAAGITLG MDELYKKLAAGSGSGYDPEGSGSGHHHHHH (SEQ ID NO: 4) |
| mCherry | MSDKIIHLTDDSFDTDVLICADGAILVDFWAEWCG PCICMIAPILDEIADEYQGKLTVAKLNIDQNPGTA PKYGIRGIPTLLLFKNGEVAATKVGALSKGQLKEF LDANLAGSGSGSDPMVSKGEEDNMAIIKEFMRFKV HMEGSVNGHEFEIEGEGEGRPYEGTQTAKLKVTKG GPLPFAWDILSPQFMYGSICAYVKHPADIPDYLIC LSFPEGFKWERVMNFEDGGVVTVTQDSSLQDGEFI YKVKLRGTNFPSDGPVMQICKTMGWEASSERMYPE DGALKGEIKQRLKLKDGGHYDAEVKTTYICAKKPV QLPGAYNVNIKLDITSHNEDYTIVEQYERAEGRHS TGGMDELYKKLAAGSGSGYDPEGSGSGHHHHHH (SEQ ID NO: 5) |

Example 1

Part (a): Synthesis of Methyl 2-(Butylthiocarbonothioylthio)Propanoate

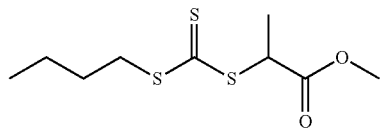

To a stirred solution of 1-butanethiol (10 mL, 0.093 mol) and TEA (14.3 mL, 0.103 mol) in DCM (100 mL) under nitrogen atmosphere was added dropwise carbon disulfide (6.18 mL, 0.103 mol) in DCM (50 mL) over a period of 30 min at 0° C. The solution gradually turned yellow during the addition. After complete addition the solution was stirred at room temperature for 1 h. MBP (11.5 mL, 0.103 mol) in DCM (50 mL) was then added dropwise to the solution over a period of 30 min, and stirred for 2 h. DCM was removed under nitrogen and the residue dissolved in diethylether. This solution was washed with cold 10% HCl solution (3×50 mL) and MilliQ water (3×50 mL) and then dried over anhydrous $MgSO_4$. The solvent was removed under vacuum and the residual yellow oil was purified by column chromatography (9:1 petroleum ether/ethyl acetate on silica, second band).

$^1$H NMR (CDCl$_3$) ppm 0.92 (tr, J=7.5 Hz, 3H, CH$_3$), 1.43 (mult, J=7.5 Hz, 2H, CH$_2$), 1.62 (d, J=7.5 Hz, 3H, CH$_3$), 1.65 (quin, J=7.5 Hz, 2H, CH$_2$), 3.36 (tr, J=7.5 Hz, 2H, CH$_2$), 3.73 (s, 3H, CH$_3$), 4.84 (quad, J=7.5 Hz, 1H, CH); $^{13}$C NMR (CDCl$_3$) □ 13.55, 16.91, 22.02, 29.89, 36.94, 47.68, 52.82, 171.63 (CH—C(=O)—O), 221.99 (S—C(=S)—S)

Part (b): Synthesis of PNIPAM$_{43}$-SC(=S)SC$_4$H$_9$ by RAFT Polymerization

NIPAM (15 g, 0.133 mol), RAFT agent (0.75 g 3.0×10$^{-3}$ mol) and AIBN (50 mg, 3.0×10$^{-4}$ mol) were dissolved in 30 ml DMSO in a 50 ml Schlenk flask. The solution was purged by Ar for 30 min. The reaction solution was then immersed in preheated oil-bath at 60° C. for 16 h. The reaction was stopped by cooling in ice-bath and exposing the solution to the air. The polymerization mixture was then diluted by 500 ml DCM and washed by Milli-Q water for three times. The organic phase was dried over MgSO$_4$, filtered, concentrated and precipitated in diethyl ether. After filtration, the yellow powder was dried under vacuum at R.T. for 48 h. ($M_{n,GPC}$=4800).

$^1$H NMR (CDCl$_3$, 298K, 500 MHz); 6.47 (b, —NH—C=O— of poly(NIPAM) repeating units), 3.97 (b, —NH—CH(CH$_3$)$_2$ of poly(NIPAM) repeating units), 4.62 (b, 1H, —CH—SC(=S)S—C$_4$H$_9$), 3.97 (b, —NH—CH(CH$_3$)$_2$ of poly(NIPAM) repeating units), 3.66 (b, 3H, CH$_3$O-RAFT residual group) 3.34 (b, 2H, —SC(=S)S—CH$_2$C$_3$H$_7$), 1.06-2.45 (b, methylene and methine protons of poly(NIPAM) backbone), 1.12 (b, methyl protons of poly(NIPAM) repeating units), 0.90 (b, 6H, methyl protons of RAFT residual group).

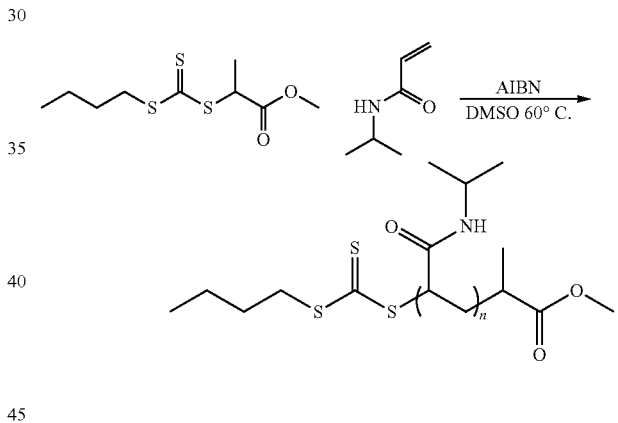

PART (c): Synthesis of Pyridine Disulfide Functionalized Poly(NIPAM)-PDS

PNIPAM$_{43}$-SC(=S)SC$_4$H$_9$ ($M_{n,GPC}$=4800, 0.29 g, 6.0×10$^{-5}$ mol), Aldrithiol™-2 (40 mg, 1.8×10$^4$ mol) and TEA (40 mg, 1.8×10$^{-4}$ mol) were dissolved in 5 ml DMF. The solution was purged by Ar for 20 min and hexylamine (40 mg, 1.8×10$^{-4}$ mol) was added via a gas-tight syringe. After stirring overnight at room temperature, the reaction mixture was blown with air line to remove some DMF. The residual was then dissolved in dichloromethane and precipitate in diethyl ether. The dissolution/precipitation operation was repeated for three times and filtered. The polymer was then dried under vacuum at room temperature for 48 h to give 0.22 g of white powdery product with yield as 75.8%.

$^1$H NMR (CDCl$_3$, 298K, 500 MHz); δ 8.45 (b, 1H, pyridine proton), 7.63 (b, 2H, pyridine protons), 7.13 (b, 1H; pyridine proton), 6.47 (b, —NH—C=O— of poly(NIPAM) repeating units), 3.97 (b, —NH—CH(CH$_3$)$_2$ of poly(NI-PAM) repeating units), 3.66 (b, 3H, CH$_3$O-RAFT residual group) 3.46 (b, 1H, methine proton close to the disulfide linkage), 1.36-2.10 (b, methylene and methine protons of poly(NIPAM) backbone), 1.12 (b, methyl protons of poly (NIPAM) repeating units), 0.88 (b, 3H, methyl protons of RAFT residual group).

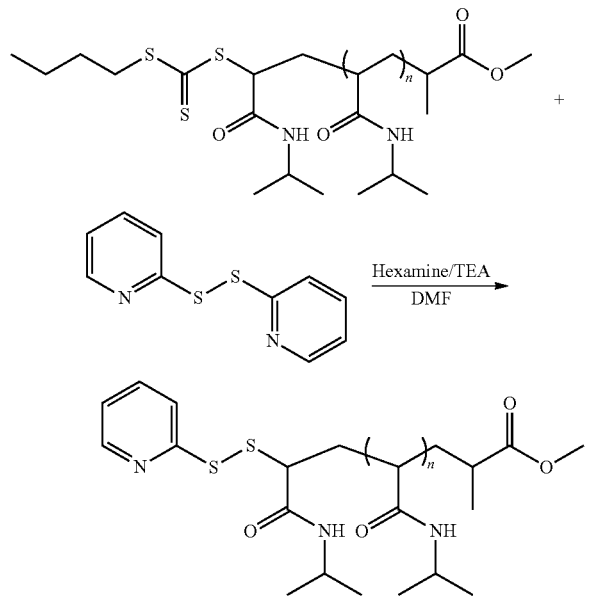

Part (d): Synthesis of Poly(NIPAM)-Protein (GFP, Cheery, Fibronectin and Vitronectin) Conjugation Recombinant proteins (GFP and mCherry) or ECM peptides (fibronectin and vitronectin) were produced as described in the literature and sequences are shown in Table 1. The PNIPAM-PDS was dissolved in Milli-Q water with a concentration of 10 mg/mL. The proteins were already in solution (at different concentrations). The PNIPAM-PDS solution was added to the protein solutions, so that a 3:1 molar ratio was achieved. The reaction mixtures were slowly shaken for 6 h at RT. The conjugation efficiency was measured by UV-Vis Spectrometry. The absorbance at 340 nm ascribed to the pyridinthione which was released out from PNIPAM-PDS after conjugate with proteins was used to quantify the conjugation efficiency. For GFP, Cherry, Fibronectin and Vitronectin, the conjugation efficiency were 100%, 97.7%, 89.6% and 28.0% respectively. The solution was then dialyzed against water for 1 day (3-times water change) and freeze-dried protein.

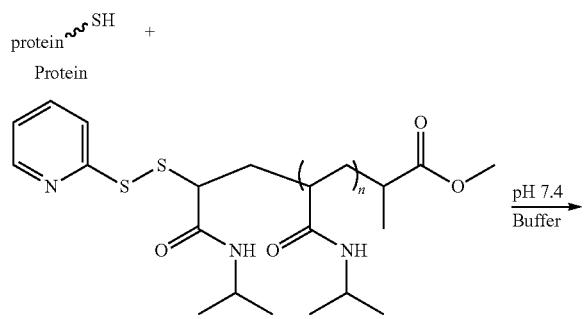

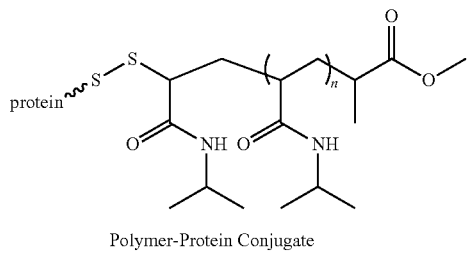

Polymer-Protein Conjugate

Part (e): RAFT-Mediated Polymerization of Styrene with PNIPAM$_{43}$-SC(=S)SC$_4$H$_9$ macroCTA and SDS in Water to Make Worms and Nanospheres A typical polymerization was performed as follows: PNIPAM$_{43}$-SC(=S)SC$_4$H$_9$ (0.350 g, $7.4 \times 10^{-5}$ mol, 5 wt %), SDS (0.0145 g, $5.0 \times 10^{-5}$ mol) and Milli-Q water (6.25 g) were added to a 10 mL Schlenk tube equipped with magnetic stirrer bar. To dissolve the polymer the solution was cooled below the LCST of PNIPAM by placing the flask in an ice bath. The polymer solution was purged with argon for 40 min. A mixture of styrene (0.350 g, $3.4 \times 10^{-3}$ mol, 5 wt %) and AIBN (0.0012 g, $7.3 \times 10^{-6}$ mol) was added with to the cooled polymer solution. The reaction mixture was purged with argon for another 10 min, and the polymerization heating in an oil bath at 70° C. for 3 h. (SEC: Mn=8300, PDI=1.10).

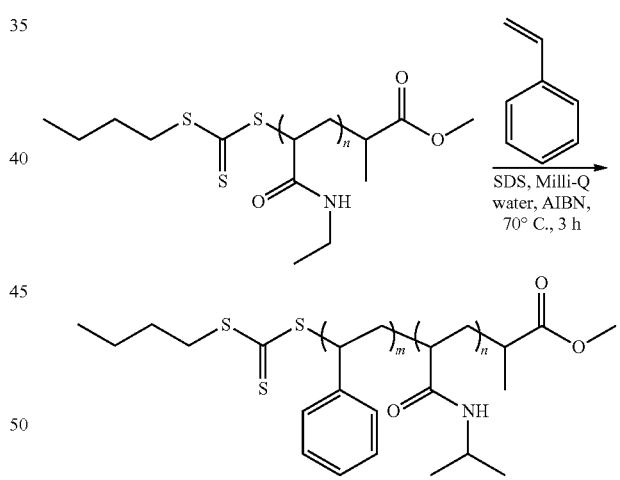

Figure 2:
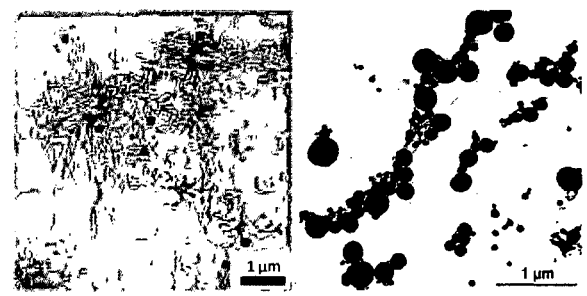
FIG. 2 illustrates TEM micrographs of polymer particles used in the invention in the form of worms (or rods) and spheres.

For making worms, 3 mL latex solution was added to a preheated glass vial with 60 µL of toluene as platicizer. The mixture was shaken for 10 seconds and then cooled down to 25° C. The polymeric worms in water was then freeze-dried to recover the powdery worms. For making the nanospheres, after polymerization the reaction vessel was open to the air to stop the reaction and continued heating at 70° C. for 4 h to remove any unpolymerized STY, monomer. The polymeric nanospheres in water were then freeze-dried to recover the powdery worms. Both the worms and nanospheres were then characterized by TEM (FIG. 2). The worm shaped structures are referred to in Example 3 as "pWorms".

Part (f): Formation of Thermo-Responsive Matrix Between PNIPAM-Protein and Worms or Nanospheres Freeze-dried worms (or nanospheres) were rehydrated with Milli-Q water at 4° C. PNIPAM-Protein solution (4° C.) was then added to the worms (or nanosphere) suspension and mixed by shaking. The solution was then heated above the LCST (29° C.) to allow the binding of PNIPAM-protein on the matrix surface of worms (or nanospheres).

Example 2

Human Embryonic Stem Cell Culture

All mammalian tissue culture reagents described here were from Life Technologies (Carlsbad, Calif., USA) unless otherwise stated. hESC lines used were NKX2-5 (eGFP/w) (hES3 background, a kind donation from Andrew Elefanty and Ed Stanley[1]), H9 (WiCell, Wisconsin, Mich., USA), MEL1 and MEL2 (referenced in[2]). NKX2-5, MEL1 and MEL2 were maintained by Stem Core Queensland and routinely supported as manually passaged cultures on MEF feeder layers as previously described[3]. Prior to experiments, cells were adapted to single cell passage as previously described[4,5] in Knockout serum replacement media containing 4 ng/mL basic fibroblast growth factor (bFGF) and 0.1 mM (3-mercaptoethanol (Sigma-Aldrich, Grand Island, N.Y., USA).

Part (a): Attachment of Human Embryonic Stem Cells to Functionalised PNIPAM/ROD Diblock Copolymers A mixture of 35 µL of pWorms (30% w/v) in PBS was combined with 35 µL of pVN or pFN in PBS (ranging from 0-50 µg of each ECM polymer conjugate). These solutions were spun coat at 4000 rpm for 30 s onto organ culture dishes (15 mm diameter tissue culture surface, BD Biosciences, Franklin Lakes, N.J., USA). Single cell suspensions of MEL1 or MEL2 cells were plated in StemPro® media at $5 \times 10^4$ cells per dish. After 2 h binding, unbound cells were washed from the surface with warm PBS at 37° C. Images were taken on an EVOSn inverted microscope (Advanced Microscopy Group, Bothell Wash.) at 20× magnification and cells counted manually[6].

Figure 3:
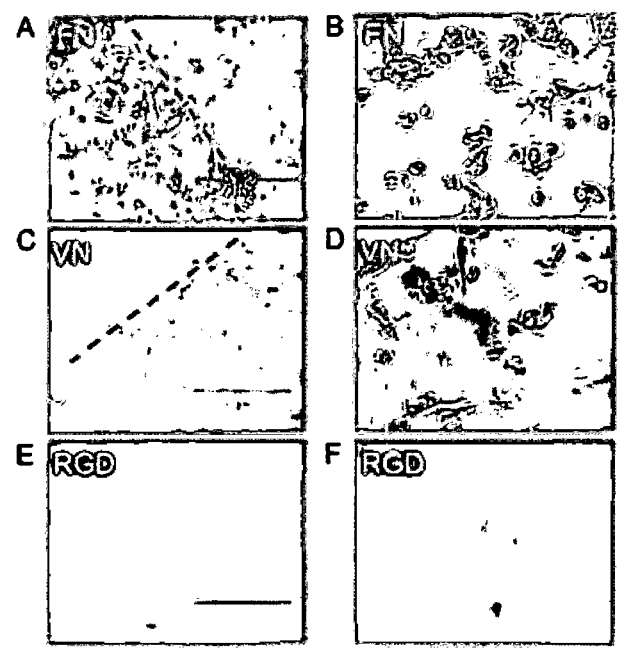
FIG. 3 illustrates protein functionalized PNIPAM/ROD surfaces support hESC cell attachment in a concentration dependent manner. (A-F) MEL1 cell binding to protein functionalised Poly(NIPAM-b-STY) diblock copolymer surfaces. (A,C) hESC binding is dependent on the Poly(NIPAM-b-STY) diblock copolymer surfaces functionalised with VN or FN as cells did not bind uncoated surfaces as indicated by the dotted line. (E and F) Poly(NIPAM-b-STY) diblock copolymer surfaces functionalised with the synthetic integrin binding peptide (RGD, up to 200 µg/well) did not support hESC attachment. (B,D,F) Higher magnification images showing the distinct cell spreading on FN and VN but not RGD. Scale bars in all images represent 400 µm. G) The number of cells bound was quantified for two independent hESC cell lines, MEL1 and MEL2 via manual cell counting of cells attached and demonstrating cell spreading over the surface. Trend lines in are log scale. Data is the average of three independent experiments.
Figure 3:
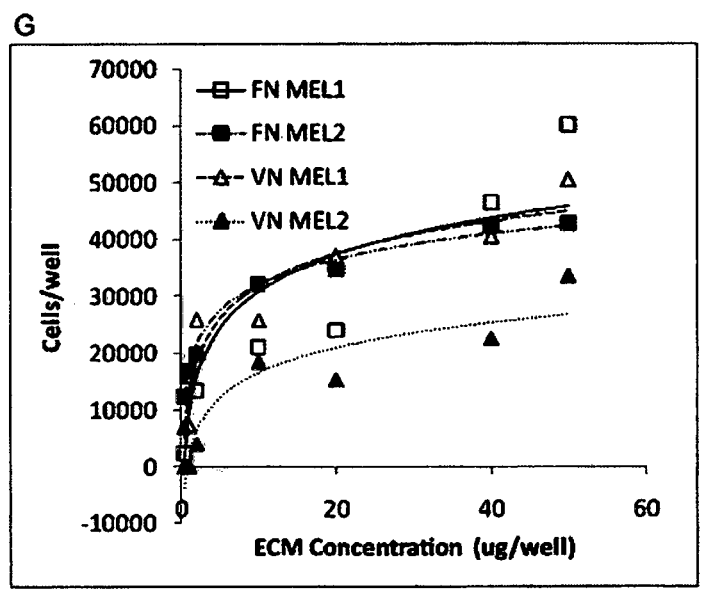

In a two component system (as in FIG. 1), the worms in water were mixed with poly(NIPAM)-protein, in which the protein was either Fibronectin, Vitronectin or the integrin binding tri-peptide RGD. Surfaces coated with either Fibronectin or Vitronectin functionalised polymer showed good attachment of hESC cell (FIG. 3A-D), whereas surfaces with RGD in this case did not (FIG. 3E-F). In addition, the number of cells attached to the functionalised polymer could be tuned by varying the concentration of the poly (NIPAM)-protein (FIG. 3G) up to 50 µg/well. With an increase in poly(NIPAM)-protein concentration, there was a corresponding increase in the number of attached cells. The combination of the worms and poly(NIPAM)-protein was essential for cell binding (FIGS. 3A and C).

Figure 4:
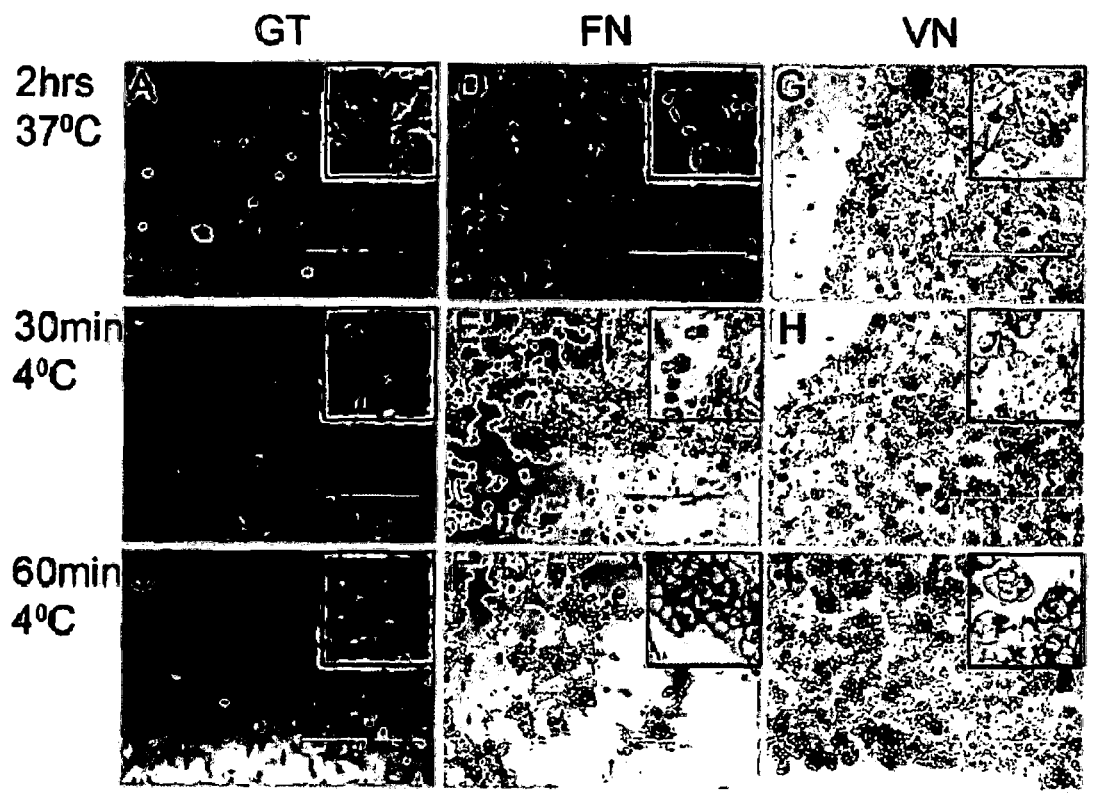
FIG. 4 illustrates the effect of temperature on hESC binding to Poly(NIPAM-b-STY) diblock copolymer surfaces functionalised with FN or VN. Light microscopy images of MEL1 cells seeded on Geltrex control surfaces (A), rVN-pNIPAM/PSTY (D) and rFN-pNIPAM/PSTY (G) glass slides at 37° C. Cultures were incubated below the LCST at 4° C. and images taken at 30 (B,E,H) and 60 min (C,F,I). For each condition, higher magnification images (inset) show cell rounding and detachment after incubation at reduced temperatures except on Geltrex™ controls (D, G). Scale bars represent 400 µm.

Part (b): Temperature Dependant, Enzyme Free Dissociation of Human Embryonic Stem Cells By decreasing the temperature below the LCST of the PNIPAM, hESC detached without the aid of enzymes, from the surface. We cultured cells for 24 h at 37° C. on Geltrex coated tissue culture plates or on glass slides coated with worms mixed with poly(NIPAM)-protein at 4° C. for 1 h. We cultured cells for 24 hours at 37° C. on Geltrex coated tissue culture plates or on glass slides coated with worms/poly (NIPAM)-protein (i.e. protein was either Fibronectin or Vitronectin). The culture was cooled to 4° C. for 1 h. Incubation of cells on Geltrex control surfaces at 4° C. had no significant impact on cell morphology with no cell rounding, a distinctive characteristic of cell detachment (FIG. 4A-C). In contrast, when cells attached to worms/poly (NIPAM)-protein surfaces were incubated below the LCST, significant cell rounding could be observed and many cells spontaneously detached from the surface (FIGS. 4D-I). Remaining cells could then be removed from the surface with gentle aspiration of the media.

Part (c): Generation of Human Embryonic Stem Cell Sheets

Figure 5:
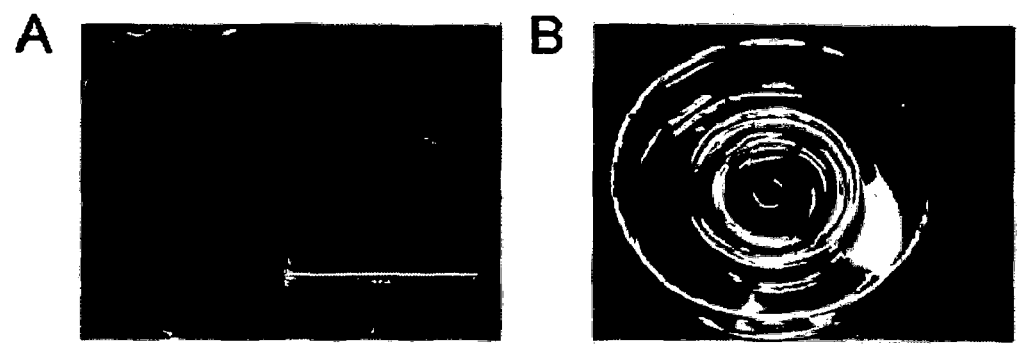
FIG. 5 illustrates detachment of hESC sheets. MEL1 cells were seeded at $1\times10^6$/well on rFN functionalized Poly(NIPAM-b-STY) diblock copolymer surfaces in organ culture dishes and incubated for 24 hours. The temperature was shifted to 25° C. and the cell sheet detached from the surface with gentle agitation. Scale bar is 1000 µm. (A) Magnified image demonstrating detachment of cell sheet periphery (dark patches). (B) Lower magnification of the cell sheet in an organ culture dish showing detachment after the incubation at room temperature.
Figure 6:
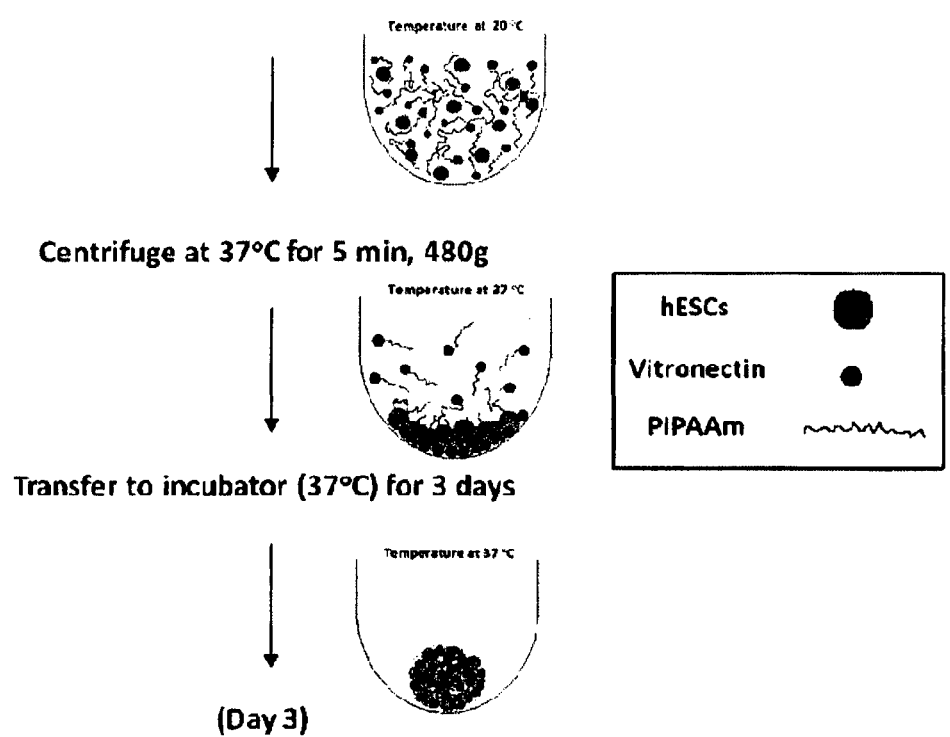
FIG. 6 illustrates a schematic representation of the formation of cell clusters according to the invention.

An organ culture dish prepared above with 50 µg of either pVN or pFN was seeded with MEL1 or MEL2 cells at $1 \times 10^6$ cells/dish, and cultured for 24 h to allow cell junctions to form. The dishes were removed from the 37° C. incubator, and left at RT (i.e. below the LCST of the PNIPAM) for 30 min to allow release of cell sheets. Cells were also seeded at low cell density ($1 \times 10^5$/dish) to further demonstrate enzyme-free detachment and released below the LCST after incubation at ~4° C. Geltrex™ (0.5% v/v in DMEM-F12) coated onto the organ culture dishes were used as the control. Incubation of these cultures at room temperature readily liberated cell sheets that could be completely removed with gentle agitation (FIG. 5). This method may enable rapid generation of small hESC clumps which are, often used in differentiation protocols. Using this method may allow generation of intact cell clumps of a defined size without the use of enzymes such as typsin and collagenase.

Example 3

Part (a): Formation and Dissociation of Human Embryonic Stem Cell Clumps (Embryoid Bodies)

hESC 3D Embryoid Body Formation with pVN and pWorms

Figure 7:
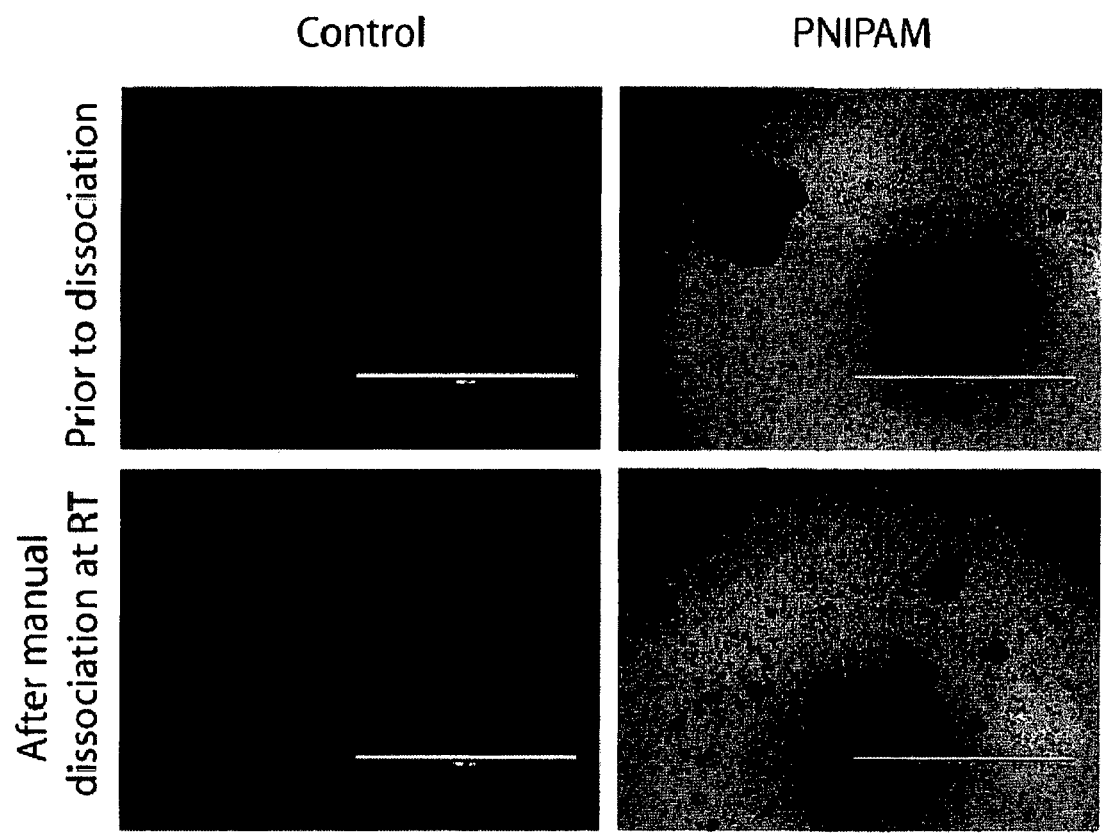
FIG. 7 illustrates dissociation of Embryoid bodies mixed with PNIPAM/ROD diblock copolymers/Vitronectin-PNIPAM. (A-B) Control and treated cell clusters prior to manual dissociation. (C-D) Dissociation of embryoid bodies into small clusters after manual titration occurs only in conditions incubated with PNIPAM/ROD diblock copolymers/Vitronectin-PNIPAM (D)

MEL1, MEL2 and NKX2-5 were used to form embryoid bodies (EB) in APEL media using the spin EB process as previously described[7] with some modifications. Briefly, 50 µL of cell suspensions containing 3500 cells were seeded per well in a round bottom 96-well plate at RT. Concentrations of pWorms (156 µg/mL), pVN (14 µg/mL) and bFGF (100 ng/mL) were added to the cell suspension. Plates were then centrifuged at 37° C. at 480 g for 5 min. Cells were incubated at 37° C. under a 5% $CO_2$ and 5% $O_2$ atmosphere. On day 3, EBs were incubated at RT for 30 min prior to gentle pipetting to break apart the EBs. FIG. 7A-B and FIG. 8B-C demonstrate that both the control cells and cells incubated with PNIPAM/ROD diblock copolymers/Vitronectin-PNIPAM were able to form embryoid bodies. However, after temperature reduction, only embryoid bodies cultured in the presence of PNIPAM/ROD diblock copolymers/Vitronectin-PNIPAM could be manually dissociated into small clusters at room temperature (FIG. 7C-D). Dissociation of EBs was scored based on 4 categories represented in FIG. 8A.

Spin EB Formation and Dissociation in the Absence of Polyvinyl Alcohol

APEL media was made as previously described except polyvinyl alcohol (PVA) was removed and the equivalent volume replaced with F-12 nutrient mix. PVA-free media was designated AEL. pWorms (0-1560 µg/mL) and pVN (0-50 µg/mL) were added to AEL media with 100 ng/mL bFGF. EBs were scored for efficient formation on day 1 based on uniformity of density, spherical EB structure and smoothness of EB boundary. Based on a dilution series of pVN and pWorm (FIG. 8D), an optimal concentration of 50 µg/mL and 1.56 ng/mL, respectively, were chosen for EB formation in the absence of PVA.

3D hESC Expansion with pVN and pWorms

Based on a dilution series of pVN and pWorms (FIGS. 8D and E), an optimal concentration of 50 µg/mL and 1.56 ng/mL, respectively, were chosen for EB formation in the absence of PVA. NKX2-5, MEL2 and H9 were used for 3D pluripotent expansion over 18 days. Media used for Spin EB, formation were AEL or StemPRO® hESC SFM[8] with and without BSA. AEL and StemPRO® hESC SFM were, supplemented with 100 and 10 ng/ml bFGF, respectively. Plates and cells were centrifuged at 37° C. at 480 g for 5 min. Cells were incubated at 37° C. under a 5% $O_2$ and 5% 02 atmosphere. EBs were gently resuspended at RT using manual pipetting to passage on days 3 and 10. Positive controls for qPCR and flow cytometry were 2D cultures either on MEF feeder layers in KSR media or feeder free in StemPRO® media on VN at 20 µg/cm[2] as described[2].

Embryoid Body (EB) Morphology and Cell Growth Kinetics

Bright field pictures of EBs were taken using an EVOSn inverted microscope (Advanced Microscopy Group) on days 10, 11 and 18. EB diameters were measured in µm using Image J (v1.41). Sixty EBs were sized per replicate per condition totaling 180 per condition. For cell counts, a selection of EBs were dissociated using TrypLE and stained with Trypan Blue for dead cell exclusion before counting on a haemocytometer.

Representative fold expansion is outlined in FIG. 9A and average EB size distribution before and after passage in FIGS. 9B and C).

Quantitative PCR

The full protocol used closely adheres to recent guidelines on conducting and reporting on qPCR results[9]. RNA extraction and DNA removal was performed using the Qiagen RNeasy RNA extraction kit (Qiagen) and on column DNASE set. Briefly, RNA was extracted from hESC at Day 18 post expansion or from differentiating cells at varying time points as indicated in figures. One microgram of DNA free RNA was converted to cDNA using Life Technologies's Superscript III First Strand Sythesis Supermix. CDNA was diluted 1:10 before qPCR. Primer sequences used for qPCR can be found in Table 2. QPCR was performed using an Applied Biosystems 7500 Fast ThermoCycler and SYBR Green Master Mix as described[10]. Primer-product specificity was confirmed by the presence of one peak in a step-wise melt curve analysis. Fold change representation was determined relative to hESC grown on MEF. All genes of interest were referenced to 3 housekeeping genes: human 0—actin, HPRT and GAPDH[11] using the Pfaffl method[12]. All experiments and qPCR runs were conducted in triplicate. Results are displayed in FIG. 9D.

TABLE 2 qPCR primer sequences

| Gene | Direction | Sequence | Size bp |
|---|---|---|---|
| B-Actin | Forward | GCT GTG CTA CGT CGC CCT G (SEQ ID NO: 6) | 61 |
| | Reverse | GGA GGA GCT GGA AGC (SEQ ID NO: 7) | |
| NANOG | Forward | CAA AGG CAA ACA ACC CAC TT (SEQ ID NO: 8) | 158 |
| | Reverse | TCT GCT GGA GGC TGA GGT AT (SEQ ID NO: 9) | |
| OCT-4 | Forward | TGA AGC TGG AGA AGG AGA AG (SEQ ID NO: 10) | 134 |
| | Reverse | ATC GGC CTG TGT ATA TCC C (SEQ ID NO: 11) | |
| GAPDH | Forward | GAA GGT GAA GGT CGG AGT CA (SEQ ID NO: 12) | 109 |
| | Reverse | AAT GAA GGG GTC ATT GAT GG (SEQ ID NO: 13) | |
| HPRT | Forward | GGGAGGCCATCACATTGTAG (SEQ ID NO: 14) | 168 |
| | Reverse | TCCCCTGTTGACTGGTCATT (SEQ ID NO: 15) | |

Flow Cytometry

Cells were fixed in 4% formalin upon dissociation and stained overnight at 4° C. with primary antibody mouse IgG1, anti-Oct-4 (2 µg/mL) (Merck Millipore). Isotype specific secondary antibody conjugated to Alexa fluor 488 was used at 1 µg/mL Expression of pluripotent marker Oct-4 was determined by flow cytometry using a C6 Accuri flow cytometer with Sampler arm (BD Biosciences). Data was analysed using CFlow Sampler software (v1.0.264.15, BD Biosciences) and results displayed in FIG. 9E.

Figure 8:
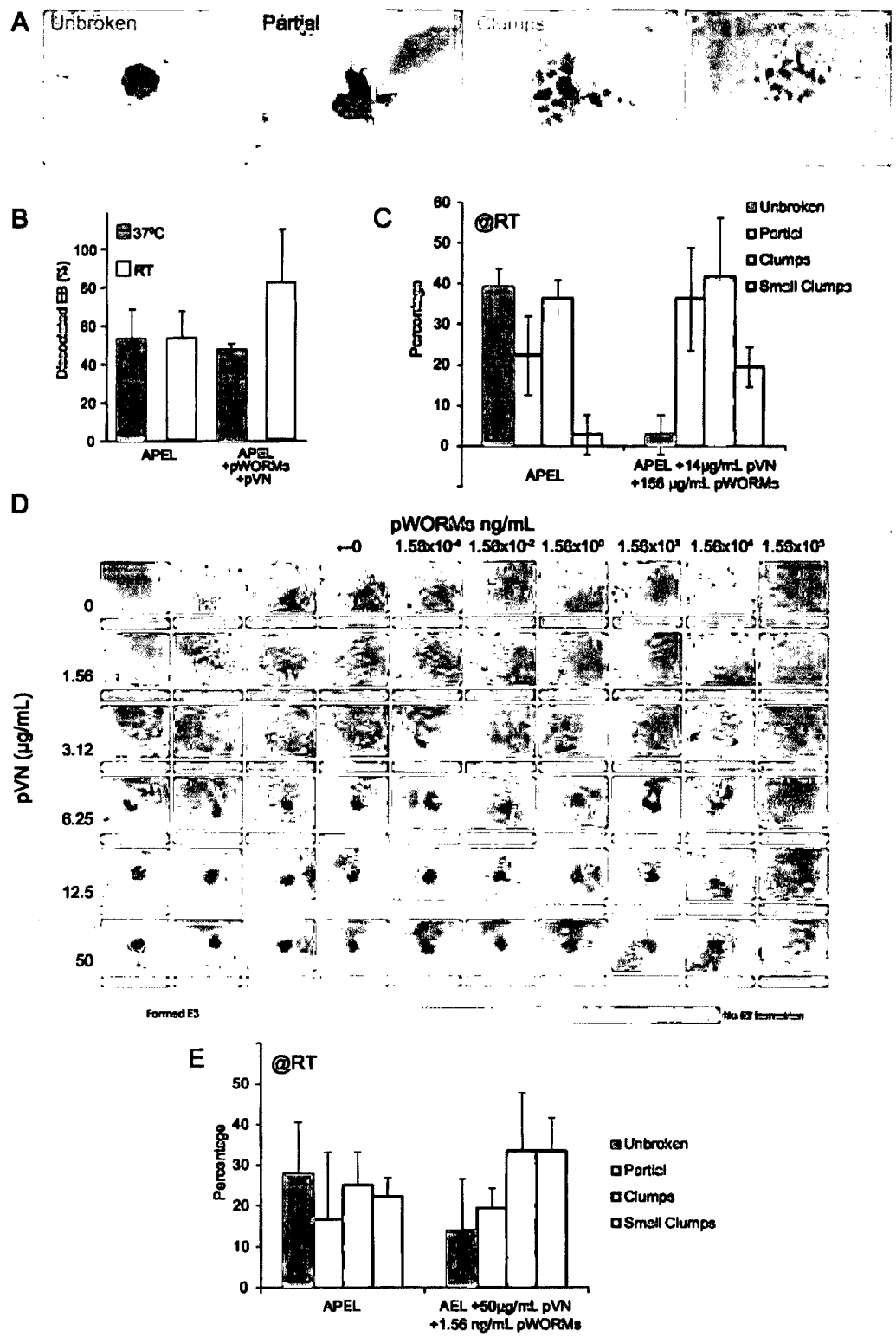
FIG. 8 illustrates data relating to a two component pNIPAM system that can be optimised to facilitate enzyme free passage of hESC embryoid bodies.
Figure 9:
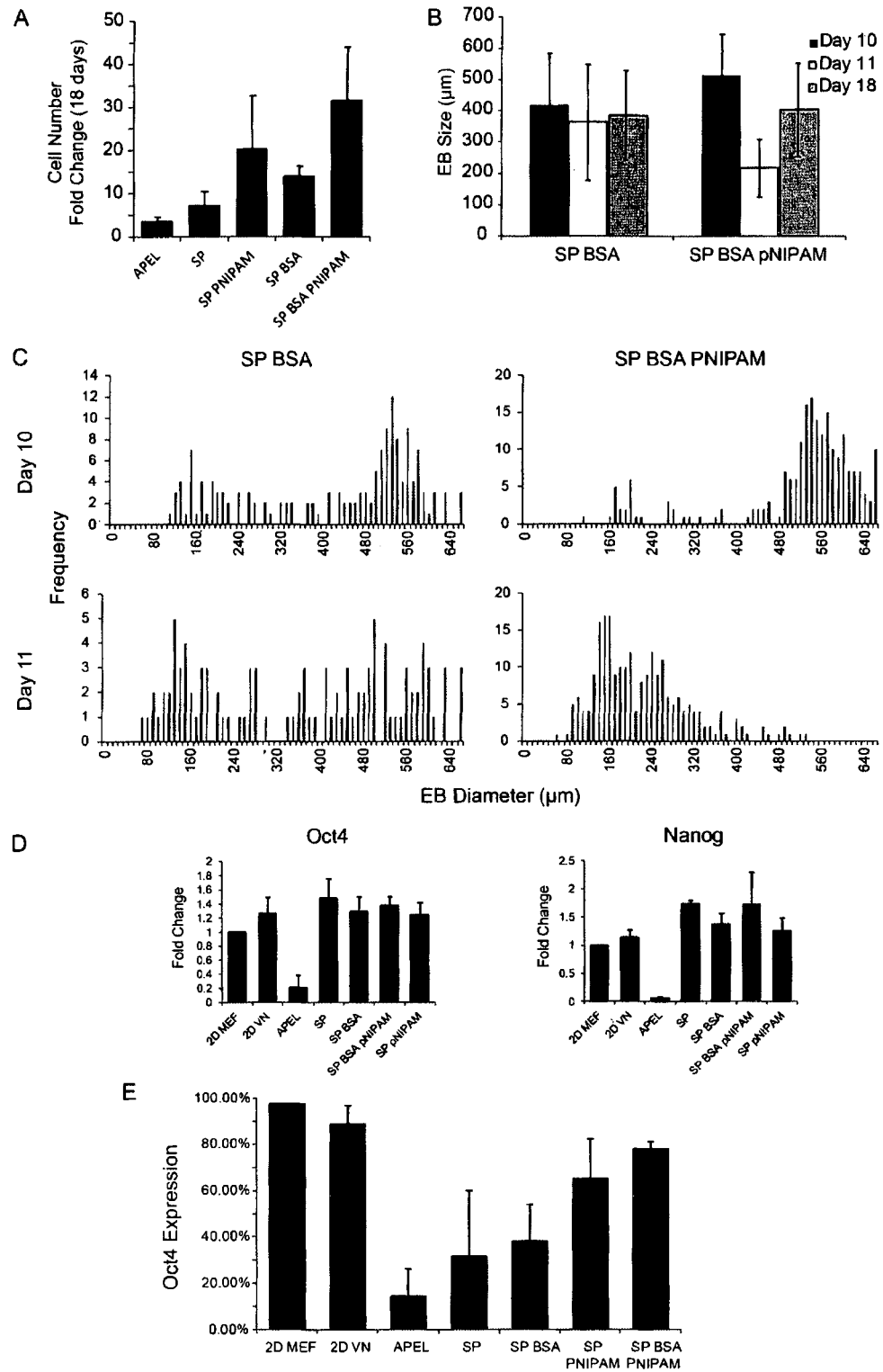
FIG. 9 illustrates data relating to pluripotent, 3D expansion of human embryonic stem cells with pNIPAM conjugates.

Further discussion relating FIGS. 8 and 9 follow:

FIG. 8—a 2 Component PNIPAM System can be Optimised to Facilitate Enzyme Free Passage of hESC Embryoid Bodies:

(A) Examples of EB clump classification after gentle manual titration at RT. EBs were formed using the Spin EB protocol in APEL media containing pWORMs (156 µg/mL) and pVN (14 µg/mL). On day 3, EBs were incubated at RT for 20 min before passing through a 200 µL pipette tip to dissociate. Scale bars are 1000 µm. (B) Percentage of broken EBs after manual dissociation. EBs were formed in APEL media with or without pWORMs/pVN as defined in A. On day 3 EBs were manually, dissociated at 37° C. or at RT and classified as broken or unbroken. (C) Distribution of EB clump size after dissociation at RT. After RT dissociation, EBs were classified according to size into four categories as outlined in A. (D) Bright field images of EBs formed during titration of pWORM and pVN in the absence of PVA. EBs were formed using the spin coat method in the absence of PVA while titrating the pWORM and pVN concentrations as shown. EBs were scored 1 to 4 on day 1 for formation based on formation of EBs (1), partial formation (2), varying clump formation (3) and no formation (4). Scores for formation were averaged across 3 independent experiments and 6 technical replicates within each experiment, n=18. (E) EB dissociation at RT in PVA free media with pWORMs and pVN. EBs formed in AEL media with pWORMs (1.56 ng/mL) and pVN (50 µg/mL) were dissociated on day 3 and classified according to EB clump sizes as outlined in (A).

APEL; Albumin Polyvinylalcohol Essential Lipids, pVN; PNIPAM-Vitronectin, AEL; Albumin Essential Lipids.

FIG. 9—Pluripotent, 3D Expansion of Human Embryonic Stem Cells with pNIPAM Conjugates:

(A) Fold expansion of Nkx2-5 hESC as embryoid bodies. EBs were formed using the spin EB method at 3,500 cells/aggregate in SP media with and without BSA and PNIPAM (pVN 50 µg/mL and pWorms 1.56 ng/mL). EBs were passaged on day 3 and 10 by incubating at RT for 20 mins followed by gentle pipetting. Fold change was based on total cell number on day 18 compared to input cell number on day 0. (B) Average EB diameter. EBs were photographed on days 10, 11 and 18. EB diameter was determined using Image J image analysis software. 60 EBs were sized per sample per replicate, n=180. (C) EB size distribution before and after passage. (D) qPCR analysis of Nanog and Oct4 gene expression. On day 18, mRNA was extracted from EBs and converted to cDNA before qPCR measurement of Oct4 and Nanog expression. Fold change is relative to hESC grown on MEF feeder layers and average using three housekeeping genes (3-actin, GAPDH and HPRT. Error bars represent standard deviation of 3 independent experiments. (E) Oct4 protein expression measured by flow cytometry. SP; StemPro, BSA; bovine serum albumin, PNIPAM; cultures with pVN 50 µg/mL and 1.56 ng/mL pWORMs, APEL; Albumin Polyvinylalcohol Essential Lipids, 2D VN; hESC on tissue culture plastic coated with vitronectin, 2D MEF; hESC grown on mouse embryonic fibroblast feeder layers.

REFERENCES

1 Elliott, D. A. et al. NKX2-5(eGFP/w) hESCs for isolation of human cardiac progenitors and cardiomyocytes. *Nat Methods* 8, 1037-1040, doi:nmeth.1740 [pii] 10.1038/nmeth.1740 (2011).
2 Prowse, A. B. et al. Long term culture of human embryonic stem cells on recombinant vitronectin in ascorbate free media. *Biomaterials* 31, 8281-8288, doi:S0142-9612(10) 00880-X [pii] 10.1016/j.biomaterials.2010.07.037 (2010).
3 Thomson, J. A. et al. Embryonic stem cell lines derived from human blastocysts. *Science* 282, 1145-1147 (1998).
4 Amit, M. et al. Human feeder layers for human embryonic stem cells. *Biol Reprod* 8, 2150-2156, doi:10.1095/biolreprod.102.012583 biolreprod.102.012583 [pii] (2003).
5 Ng, E. S., Davis, R. P., Hatzistavrou, T., Stanley, E. G. & Elefanty, A. G. Directed differentiation of human embryonic stem cells as spin embryoid bodies and a description of the hematopoietic blast colony forming assay. *Curr Protoc Stem Cell Biol* Chapter 1, Unit 1D 3, doi:10.1002/9780470151808.sc01d03s4 (2008).
6 Mizutani, A., Kikuchi, A., Yamato, M., Kanazawa, H. & Okano, T. Preparation of thermoresponsive polymer brush surfaces and their interaction with cells. *Biomaterials* 29, 2073-2081, doi:10.1016/j.biomaterials.2008.01.004 (2008).
7 Ng, E. S., Davis, R., Stanley, E. G. & Elefanty, A. G. A protocol describing the use of a recombinant protein-based, animal product-free medium (APEL) for human embryonic stem cell differentiation as spin embryoid bodies. *Nat Protoc* 3, 768-776, doi:nprot.2008.42 [pii] 10.1038/nprot.2008.42 (2008).
8 Wang, L. et al. Self-renewal of human embryonic stem cells requires insulin-like growth factor-1 receptor and ERBB2 receptor signaling. *Blood* 110, 4111-4119, doi: blood-2007-03-082586 [pii] 10.1182/blood-2007-03-082586 (2007).
9 Bustin, S. A. et al. The MIQE guidelines: minimum information for publication of quantitative real-time PCR experiments. *Clin Chem* 55, 611-622, doi: clinchem.2008.112797 [pii] 10.1373/clinchem.2008.112797 (2009).
10 Prowse, A. B. et al. Analysis of mitochondrial function and localisation during human embryonic stem cell differentiation in vitro. *PLoS One* 7, e52214, doi:10.1371/journal.pone.0052214 PONE-D-12-24905 [pii] (2012).
11 Vandesompele, J. et al. Accurate normalization of real-time quantitative RT-PCR data by geometric averaging of multiple internal control genes. *Genome Biol* 3, RESEARCH0034 (2002).
12 Pfaffl, M. W. A new mathematical model for relative quantification in real-time RT-PCR. *Nucleic Acids Res* 29, e45 (2001).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A composition comprising polymer particles and functionalised stimulus responsive polymer;
the polymer particles (i) comprising block co-polymer, and (ii) having a core-shell structure, said block co-polymer comprising (a) a non-stimulus responsive polymer block that forms at least part of the core structure, and (b) a stimulus responsive polymer block that forms at least part of the shell structure;
wherein the stimulus responsive polymer of both the polymer particles and the functionalised stimulus responsive polymer are responsive to at least one common stimulus.

2. The composition according to claim 1 further comprising a liquid, wherein the stimulus responsive polymer associated with both the polymer particles and the functionalised stimulus responsive polymer are soluble within the liquid.

3. The composition according to claim 1 further comprising a liquid and being in the form of a gel, wherein the stimulus responsive polymer associated with both the polymer particles and the functionalised stimulus responsive polymer are insoluble within the liquid.

4. A cell culture system comprising the composition according to claim 1.

5. A drug delivery system comprising the composition according to claim 1.

6. A method of culturing cells, said method comprising:
(i) providing a liquid composition comprising polymer particles and cell functionalised stimulus responsive polymer;
the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;
wherein the stimulus responsive polymer of both the polymer particles and the cell functionalised stimulus responsive polymer are (a) responsive to at least one common stimulus, and (b) soluble in the liquid;
(ii) subjecting the liquid composition to said common stimulus so as to cause the stimulus responsive polymer of both the polymer particles and the cell functionalised stimulus responsive polymer to transition from being soluble in the liquid to being insoluble in the liquid, wherein said transition promotes aggregation of the polymer particles and the cell functionalised stimulus responsive polymer to form cell clusters; and
(iii) culturing cells within and/or on said cell clusters.

7. The method according to claim 6 further comprising a step of:
(iv) subjecting the liquid composition comprising the cultured cells to said common stimulus so as to cause the stimulus responsive polymer of both the polymer particles and the cell functionalised stimulus responsive polymer to transition from being insoluble in the liquid to being soluble in the liquid, wherein said transition facilitates release from said cell clusters of individual cells and/or smaller cell clusters.

8. The method according to claim 7 further comprising a step of:
(v) removing from the liquid composition at least some of the so formed individual cells and/or smaller cell clusters formed in step (iv).

9. The method according to claim 6, wherein the liquid is an aqueous liquid and the stimulus responsive polymer of both the polymer particles and the cell functionalised stimulus responsive polymer is a thermoresponsive polymer having a common LCST.

10. The method according to claim 9, wherein said common stimulus applied in step (ii) is increasing the temperature of the liquid above the LCST.

11. The method according to claim 9, wherein 37° C. is at or above the LCST.

12. A method of culturing cells, said method comprising:
(i) providing a liquid composition comprising, a liquid, cell receptor ligand functionalised stimulus responsive polymer and polymer particles secured to a substrate;
the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;
wherein the stimulus responsive polymer of both the polymer particles and the cell receptor ligand functionalised stimulus responsive polymer are (a) responsive to at least one common stimulus, and (b) soluble in the liquid;
(ii) subjecting the liquid composition to said common stimulus so as to cause the stimulus responsive polymer of both the polymer particles and the cell receptor ligand functionalised stimulus responsive polymer to transition from being soluble in the liquid to being insoluble in the liquid, wherein said transition promotes aggregation of the polymer particles and the cell receptor ligand functionalised stimulus responsive polymer to form an aggregate structure with a surface comprising the cell receptor ligand;
(iii) introducing to the liquid one or more cells that are to be cultured such that it or they bind with a cell receptor ligand; and
(iv) culturing cells upon said surface comprising the cell receptor ligand.

13. The method according to claim 12 further comprising a step of:
(v) subjecting the liquid composition comprising the cultured cells to said common stimulus so as to cause the stimulus responsive polymer of both the polymer particles and the cell receptor ligand functionalised stimulus responsive polymer to transition from being insoluble in the liquid to being soluble in the liquid, wherein said transition facilitates release of said cultured cells.

14. The method according to claim 13 further comprising a step of:
(vi) removing from the liquid composition at least some of the cultured cells formed in step (v).

15. The method according to claim 12, wherein the liquid is an aqueous liquid and the stimulus responsive polymer of both the polymer particles and the cell receptor ligand functionalised stimulus responsive polymer is a thermoresponsive polymer having a common LCST.

16. The method according to claim 15, wherein said common stimulus applied in step (ii) is increasing the temperature of the liquid composition above the LCST.

17. The method according to claim 15, wherein said common stimulus applied in step (v) is decreasing the temperature of the liquid composition below the LCST.

18. The method according to claim 15, wherein 37° C. is at or above the LCST.

19. A method of forming a gel comprising functionalised stimulus responsive polymer, said method comprising:

(i) providing a liquid composition comprising a liquid, polymer particles and functionalised stimulus responsive polymer;

the polymer particles (a) comprising block co-polymer, and (b) having a core-shell structure, said block co-polymer comprising (a) a non-stimulus responsive polymer block that forms at least part of the core structure, and (b) a stimulus responsive polymer block that forms at least part of the shell structure;

wherein the stimulus responsive polymer of both the polymer particles and the functionalised stimulus responsive polymer are (a) responsive to at least one common stimulus, and (b) soluble in the liquid; and (ii) subjecting the liquid composition to said common stimulus so as to cause the stimulus responsive polymer of both the polymer particles and the functionalised stimulus responsive polymer to transition from being soluble in the liquid to being insoluble in the liquid, wherein said transition promotes formation of the gel.

20. A method of releasing from a gel a functionalised stimulus responsive polymer, said method comprising:

(i) providing a gel comprising polymer particles, a functionalised stimulus responsive polymer and liquid;

the polymer particles (a) comprising block co-polymer, and (b) having a core-shell structure, said block co-polymer comprising (a) a non-stimulus responsive polymer block that forms at least part of the core structure and (b) a stimulus responsive polymer block that forms at least part of the shell structure;

wherein the stimulus responsive polymer of both the polymer particles and the functionalised stimulus responsive polymer are (a) responsive to at least one common stimulus, and (b) insoluble in the liquid; and (ii) subjecting the gel to said common stimulus so as to cause the stimulus responsive polymer of both the polymer particles and the functionalised stimulus responsive polymer to transition from being insoluble in the liquid to being soluble in the liquid, wherein said transition causes the gel to become a liquid composition comprising the polymer particles and the functionalised stimulus responsive polymer, thereby promoting release of the functionalised stimulus responsive polymer from the gel.

* * * * *